United States Patent
Derwin et al.

(10) Patent No.: US 10,004,586 B2
(45) Date of Patent: Jun. 26, 2018

(54) BIOCOMPATIBLE TISSUE GRAFT

(71) Applicant: The Cleveland Clinic Foundation, Cleveland, OH (US)

(72) Inventors: Kathleen Anne Derwin, Shaker Heights, OH (US); Anthony Calabro, Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 279 days.

(21) Appl. No.: 14/837,658

(22) Filed: Aug. 27, 2015

(65) Prior Publication Data
US 2016/0058534 A1    Mar. 3, 2016

Related U.S. Application Data
(60) Provisional application No. 62/042,567, filed on Aug. 27, 2014.

(51) Int. Cl.
*A61F 2/02*  (2006.01)
*A61F 2/00*  (2006.01)
(Continued)

(52) U.S. Cl.
CPC ............ *A61F 2/0063* (2013.01); *A61L 27/34* (2013.01); *A61L 27/3633* (2013.01); *A61L 27/52* (2013.01);
(Continued)

(58) Field of Classification Search
CPC .. A61F 2/00; A61F 2/02; A61F 2/0063; A61L 27/34; A61L 27/52; A61L 27/3633
See application file for complete search history.

(56) References Cited

U.S. PATENT DOCUMENTS
5,527,893 A    6/1996    Burns et al.
6,537,979 B1    3/2003    Kuo et al.
(Continued)

FOREIGN PATENT DOCUMENTS
| WO | 2003007787 A2 | 1/2003 |
| WO | 2013127374 A1 | 9/2013 |
| WO | 2014/105875 A1 | 7/2014 |

OTHER PUBLICATIONS
Brochhausen C. et al. "Intraperitoneal adhesions—An ongoing challenge between biomedical engineering and the life sciences," J Biomed Mater Res Part A; 2011; 98A: 143-156.
(Continued)

*Primary Examiner* — Victor Nguyen
(74) *Attorney, Agent, or Firm* — Pearne & Gordon LLP

(57) ABSTRACT

Biocompatible tissue grafts are provided. The biocompatible tissue grafts include a bulk graft including a biocompatible material and having at least a first surface. The biocompatible tissue grafts also include a coating including a hydrogel and being immobilized on the bulk graft at the first surface. The biocompatible material includes at least one of a biologic material or a biologic-synthetic composite material. The hydrogel includes cross-linked hydroxyphenyl-substituted hyaluronan (HPS-HA), cross-linked hydroxyphenyl-substituted collagen (HPS-C), or both. The cross-linked HPS-HA, cross-linked HPS-C, or both have been formed by cross-linking of hydroxyphenyl groups of HPS-HA, HPS-C, or both to form dihydroxyphenyl bridges. Also disclosed are methods for repair of tissue damage in a subject in need thereof. The methods include surgically implanting the biocompatible tissue graft into a site of the tissue damage in the subject.

29 Claims, 5 Drawing Sheets
(5 of 5 Drawing Sheet(s) Filed in Color)

(51) Int. Cl.
*A61L 27/36* (2006.01)
*A61L 27/52* (2006.01)
*A61L 27/34* (2006.01)
*A61L 31/10* (2006.01)
*A61L 31/14* (2006.01)

(52) U.S. Cl.
CPC .............. *A61L 31/10* (2013.01); *A61L 31/145* (2013.01); *D10B 2509/08* (2013.01)

(56) References Cited

U.S. PATENT DOCUMENTS

| | | | |
|---|---|---|---|
| 6,790,438 | B1 | 9/2004 | Constancis et al. |
| 6,982,298 | B2 | 1/2006 | Calabro et al. |
| 7,651,702 | B2 | 1/2010 | Wang |
| 8,080,260 | B2 | 12/2011 | Derwin et al. |
| 8,207,262 | B2 | 6/2012 | Calabro et al. |
| 8,410,180 | B2 | 4/2013 | Calabro et al. |
| 2005/0220848 | A1* | 10/2005 | Bates .................. A61F 2/06 424/443 |
| 2009/0142309 | A1* | 6/2009 | Calabro ............. C08B 37/0072 424/93.7 |
| 2009/0186077 | A1 | 7/2009 | Ying et al. |
| 2009/0204227 | A1 | 8/2009 | Derwin et al. |
| 2012/0070433 | A1 | 3/2012 | Kurisawa et al. |
| 2013/0116799 | A1 | 5/2013 | Derwin et al. |

OTHER PUBLICATIONS

Bruggeman L.A. et al. "A cell culture system for the structure and hydrogel properties of basement membranes; Application to capillary walls," Cellular and Molecular Bioengineering; 2012; 5(2): 194-204 (available in PMC Jun. 1, 2013 as pp. 1-17).

Chin L. et al. "Characterization of and host response to tyramine substituted-hyaluronan enriched fascia extracellular matrix," Journal of Materials Science: Materials in Medicine; 2011; 22:1465-1477.

Darr A. et al. "Synthesis and characterization of tyramine-based hyaluronan hydrogels," Journal of Materials Science Materials in Medicine; 2009; 20(1):33-44.

Deeken C.R. et al. "A review of the composition, characteristics, and effectiveness of barrier mesh prostheses utilized for laparoscopic ventral hernia repair," Surgical Endoscopy; 2012; 26:566-575.

Deeken C.R. et al. "Physicomechanical Evaluation of Polypropylene, Polyester, and Polytetrafluoroethylene Meshes for Inguinal Hernia Repair," J Am Coll Surg; 2011; 212(1); 68-79.

Kurisawa M. et al. "Injectable biodegradable hydrogels composed of hyaluronic acid-tyramine conjugates for drug delivery and tissue engineering," Chemical Communications; 2005(34): 4312-4314.

Lee F. et al. "An injectable hyaluronic acid-tyramine hydrogel system for protein delivery," Journal of Controlled Release; 2009; 134(3): 186-193.

International Search Report and Written Opinion from Corresponding Application No. PCT/US2015/047208; Dated Oct. 30, 2015.

FDA, Summary of Safety and Effectiveness Data for FocalSeal-L Synthetic Absorbable Sealant, 2000, pp. 1-14 (upper right corner), available at https://www.accessdata.fda.gov/cdrh_docs/pdf/P990028b.pdf (accessed Oct. 6, 2017).

* cited by examiner (A)

(B)

BIOCOMPATIBLE TISSUE GRAFT

CROSS-REFERENCE TO RELATED APPLICATIONS

This application claims the benefit of U.S. Provisional Application No. 62/042,567, filed Aug. 27, 2014, the entire disclosure of which is hereby incorporated herein by reference.

STATEMENT OF GOVERNMENT-SPONSORED RESEARCH

This invention was made with government support under AR056633 awarded by the National Institutes of Health. The government has certain rights in the invention.

FIELD OF THE INVENTION

The present invention relates generally to biocompatible tissue grafts, and, more particularly, to biocompatible tissue grafts comprising (a) a bulk graft comprising a biocompatible material and having at least a first surface, and (b) a coating comprising a hydrogel and being immobilized on the bulk graft at the first surface.

BACKGROUND OF THE INVENTION

Ventral abdominal wall hernias occur in nearly one-third of the over two million patients undergoing laparotomies in the United States each year. These hernias not only affect patient quality of life through pain and discomfort, but can also cause life-threatening visceral incarceration and strangulation. An estimated 350,000 ventral hernia repairs are performed annually, involving a total cost of US $3.2 billion (2006 data). Despite advances in repair techniques and availability of a wide variety of synthetic and biological grafts, hernia repairs continue to rise in incidence and cost, with 24-43% of repairs failing to heal. Biologic grafts are recommended in hernia patients with bacterial contamination or high risk wounds, and are also preferred in laparoscopic ventral hernia repair requiring intraperitoneal placement of the graft. However, biologic grafts often lose strength and integrity after implantation, and undergo stretching, thinning and premature failure, resulting in repair bulging, dehiscence and hernia recurrence. Currently, the mechanisms for premature biological graft resorption are unknown, but likely involve a combination of patient clinical factors, surgical technique, and graft-related factors that affect cellular response and ultimately graft fate.

BRIEF SUMMARY OF THE INVENTION

In one example aspect, a biocompatible tissue graft is provided. The biocompatible tissue graft comprises a bulk graft. The bulk graft comprises a biocompatible material and has at least a first surface. The biocompatible tissue graft also comprises a coating. The coating comprises a hydrogel and is immobilized on the bulk graft at the first surface. The biocompatible material comprises at least one of a biologic material or a biologic-synthetic composite material. The hydrogel comprises cross-linked hydroxyphenyl-substituted hyaluronan (also termed HPS-HA), cross-linked hydroxyphenyl-substituted collagen (also termed HPS-C), or both, the cross-linked HPS-HA, cross-linked HPS-C, or both having been formed by cross-linking of hydroxyphenyl groups of HPS-HA, HPS-C, or both to form dihydroxyphenyl bridges.

In another example aspect, a method of repair of tissue damage in a subject in need thereof is provided. The method comprises surgically implanting a biocompatible tissue graft into a site of the tissue damage in the subject. The biocompatible tissue graft is as described above. Accordingly, the biocompatible tissue graft comprises a bulk graft. The bulk graft comprises a biocompatible material and has at least a first surface. The biocompatible tissue graft also comprises a coating. The coating comprises a hydrogel and is immobilized on the bulk graft at the first surface. The biocompatible material comprises at least one of a biologic material or a biologic-synthetic composite material. The hydrogel comprises cross-linked HPS-HA, cross-linked HPS-C, or both, the cross-linked HPS-HA, cross-linked HPS-C, or both having been formed by cross-linking of hydroxyphenyl groups of HPS-HA, HPS-C, or both to form dihydroxyphenyl bridges.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other aspects of the present invention will become apparent to those skilled in the art to which the present invention relates upon reading the following description with reference to the accompanying drawings.

DETAILED DESCRIPTION OF THE INVENTION

Figure 1:
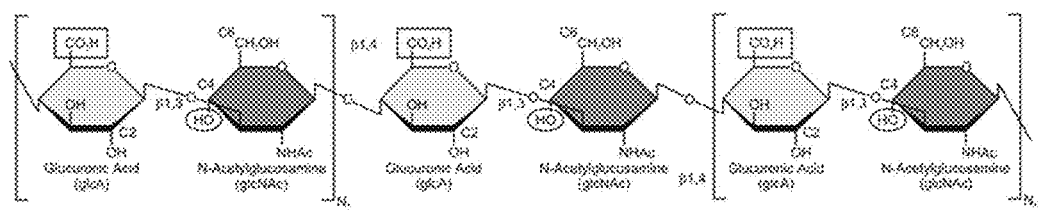
FIG. 1 shows the chemical structure of hyaluronan, which is composed of repeating pairs of glucuronic acid (glcA) and N-acetylglucosamine (glcNAc) residues linked by a $\beta1,3$ glycosidic bond.

We have determined that HPS-HA and/or HPS-C can be used to form a coating of a biocompatible tissue graft to improve graft durability and reduce premature resorption in the context of soft tissue repair. The HPS-HA and/or HPS-C can be added to the surface of a bulk graft comprising a biocompatible material comprising a biologic material and/or biologic-synthetic composite material, then cross-linked, to create the coating. The cross-linking causes the HPS-HA and/or HPS-C to gel at the surface of the bulk graft. The degree of hydroxyphenyl substitution and extent of cross-linking of the HPS-HA and/or HPS-C can be used to control the rate of bulk graft resorption and/or coating persistence, thereby reducing premature resorption and improving graft durability.

One of our contributions is to define the relationship between juxtaposition of a biocompatible tissue graft including the coating and permissiveness of the graft to various mesenchymal tissues with respect to cell and remodeling fate, and then to use the resulting data to inform a strategy to improve biologic graft durability leading to successful outcomes in hernia repair. This is significant for developing strategies to engineer durability into biologic grafts as the primary modifiable factor for reducing premature resorption in soft tissue repair. Given that patient and surgical factors drive the complexity of hernia repair, yet offer limited opportunity for modification, a durable biologic graft may mitigate the influence of these factors on clinical outcomes and give more surgeons a tool to successfully repair even complex ventral hernias that would otherwise be left to only the most specialized in their field. An engineered graft that can reduce the incidence of complications and reherniation commonly associated with currently available biologic grafts would improve outcomes, reduce reintervention, and reduce healthcare costs (1% reduction in hernia recurrence is estimated to result in a cost saving of US $32 million) for patients with complex ventral hernias. Furthermore, a strategy to engineer biologic grafts with improved durability could be translated to other clinical indications of soft tissue repair where grafts are commonly used with limited success, such as for example rotator cuff repair, pelvic organ prolapse or uro-gynecological reconstruction. In addition, what is learned will broaden our understanding of how biologic biomaterials interact with their local tissue environment, thus guiding their preferred surgical placement in proximity to mesenchymal tissues in different clinical scenarios.

Grafts derived from human acellular dermis matrix (also termed HADM) are used in hernia repair due to their ability to be used in contaminated fields and their abdominal wall-like de novo mechanical properties. However, inherent variability and poor long-term durability of HADM result in the repair prematurely losing mechanical strength and integrity, and manifest as repair bulging, dehiscence and hernia recurrence in many patients. Chemical cross-linking of endogenous collagen has been used to increase durability of biologic grafts. However, such cross-linking also alters the extracellular matrix structure and may inhibit cellular infiltration, revascularization and integration with host tissues, resulting in adverse events such as severe foreign body reaction, acute mechanical failure and disintegration of the graft. Our work presents a novel and translatable approach of using biocompatible hyaluronan (also termed HA) and/or collagen surface coatings to confer consistency in graft presentation and permissiveness to cellular infiltration from host tissue for fundamental studies, and subsequently as a strategy to engineer graft fate and clinical outcomes in ventral hernia repair. Our work also provides planar biaxial biomechanical testing of an entire repair construct. We expect that our method will allow discrimination of important and predictive subclinical differences in repair function even prior to the manifestation of clinically discernible differences, allowing hernia repair studies in animal models within practical timeframes. By demonstrating a strategy to overcome the current durability limitations of biologic tissue grafts, our work also may establish a platform to expand the indications and use of biologic grafts in a variety of soft tissue repair applications.

As noted above, in one example aspect, a biocompatible tissue graft is provided. The biocompatible tissue graft can be, for example, a soft tissue graft, a mesenchymal tissue graft, a hernia repair graft, a rotator cuff repair graft, a pelvic organ prolapse repair graft, or a uro-gynecological reconstruction graft.

The biocompatible tissue graft comprises a bulk graft. The bulk graft forms the core of the biocompatible tissue graft. The bulk graft can have a material structure corresponding to, for example, a sheet, a strip, a mesh, a weave, a melt, or a combination thereof, among other material structures.

The bulk graft comprises a biocompatible material. The biocompatible material comprises at least one of a biologic material or a biologic-synthetic composite material. The biologic material or biologic-synthetic composite material of the biocompatible tissue graft can comprise, for example, at least one of an extracellular matrix material, acellular dermis matrix, non-reinforced acellular dermis matrix, reinforced acellular dermis matrix, decellularized small intestinal submucosa, urinary bladder matrix, muscle, fibronectin, fibrin, fibrinogen, collagen, adhesive glycoprotein, proteoglycan, heparin sulfate, chondroitin sulfate, dermatan sulfate, hyaluronan, secreted protein acidic and rich in cysteine (SPARC), thrombospondins, tenacin, a cell adhesion molecule, integrin, vitronectin, fibronectin, laminin, elastin, protein found in basement membranes, fibrosin, albumin, sodium alginate, a derivative of sodium alginate, chitosan, a derivative of chitosan, gelatin, starch, silk, cellulose, methylcellulose, hydroxypropylcellulose, hydroxypropylmethylcellulose, carboxymethylcellulose, cellulose acetate phthalate, cellulose acetate succinate, hydroxypropylmethylcellulose phthalate, casein, dextran, a derivative of dextran, polysaccharides, poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), polypropylene (PP), polyurethane (PU), expanded polytetrafluoroethylene (ePTFE), polylactic acid (PLA), polyglycolic acid (PGA), polycaprolactone (PCL), polydioxanone (PDO), trimethylene carbonate (TMC), polyvinyl alcohol (PVA), poly(ethylene oxide), poly(acrylic acid), poly(vinyl alcohol), poly(N-isopropyl acrylamide), poly(vinyl pyrrolidone) (PVP), poly(methacrylic acid), poly(p-styrene carboxylic acid), poly(p-styrenesulfonic acid), poly(vinylsulfonicacid), poly(ethyleneimine), poly(vinylamine), poly(anhydride), poly(HEMA), polyhydroxybutyrate (PHB), copolymers of two or more of the polymers above, or blends of two or more of the polymers above. For example, the biologic material or biologic-synthetic composite material can comprise at least one of human extracellular matrix material, human acellular dermis matrix, non-reinforced human acellular dermis matrix, or reinforced human acellular dermis matrix.

The bulk graft can have a physical structure similar to that of the biologic material, or of the biologic component of the biologic-synthetic composite material. For example, human acellular dermis matrix can have (i) a thickness of 0.5 to 4.0 mm, e.g. 0.7 to 3.0 mm, 0.9 to 2.0 mm, or about 1.4 mm, (ii) occasional voids corresponding to tracks made by hair follicles, nerves, glands, blood vessels and/or lymph vessels, on the order of 100 μm or less in diameter, and/or (iii) a density of 0.2 g/cm$^3$ to 0.6 g/cm$^3$, 0.3 g/cm$^3$ to 0.5 g/cm$^3$, or about 0.4 g/cm$^3$. Thus, the bulk graft can have at least one of (i) a thickness of 0.5 to 4.0 mm, e.g. 0.7 to 3.0 mm, 0.9 to 2.0 mm, or about 1.4 mm, (ii) occasional voids corresponding to tracks made by hair follicles, nerves, glands, blood vessels and/or lymph vessels, of approximately 100 μm or less in diameter, or (iii) a density of 0.2 g/cm$^3$ to 0.6 g/cm$^3$, 0.3 g/cm$^3$ to 0.5 g/cm$^3$, or about 0.4 g/cm$^3$.

The bulk graft has at least a first surface. The first surface can be, for example, a first major surface of the bulk graft, e.g. for a bulk graft having a flat, elongated form. The first surface also can be, for example, a portion of a first major surface of the bulk graft, e.g. for a bulk graft having a flat, elongated form and of which the first major surface is heterogeneous.

The biocompatible tissue graft also comprises a coating. The coating comprises a hydrogel, e.g. a three-dimensional network of hydrophilic polymer molecules that is highly water absorbent (e.g. hydrated or hydratable) and that can be in a wet state (e.g. containing water) or a dry state (e.g. lyophilized). The hydrogel comprises cross-linked HPS-HA, cross-linked HPS-C, or both, the cross-linked HPS-HA, cross-linked HPS-C, or both having been formed by cross-linking of hydroxyphenyl groups of HPS-HA, HPS-C, or both to form dihydroxyphenyl bridges. Thus, in some examples the hydrogel comprises cross-linked HPS-HA. Also, in some examples the hydrogel comprises cross-linked HPS-C. Also, in some examples the hydrogel comprises both cross-linked HPS-HA and cross-linked HPS-C. Moreover, considering these examples in more detail, in some aspects the hydrogel comprises cross-linked HPS-HA and not cross-linked HPS-C. Also in some aspects, the hydrogel comprises cross-linked HPS-C and not cross-linked HPS-HA. Also in some aspects, the hydrogel comprises both cross-linked HPS-HA and cross-linked HPS-C, the cross-linked HPS-HA and the cross-linked HPS-C being co-distributed within the hydrogel. Also, in some aspects the hydrogel comprises both cross-linked HPS-HA and cross-linked HPS-C, the cross-linked HPS-HA and the cross-linked HPS-C not being co-distributed within the hydrogel.

As noted, the hydrogel comprises cross-linked HPS-HA, cross-linked HPS-C, or both, the cross-linked HPS-HA, cross-linked HPS-C, or both having been formed by cross-linking of hydroxyphenyl groups of HPS-HA, HPS-C, or both to form dihydroxyphenyl bridges.

Cross-linked HPS-HA, cross-linked HPS-C, or both can be prepared in two steps, as previously described (e.g. U.S. Pat. No. 6,982,298, which is incorporated herein by reference). The first step comprises covalent coupling of a plurality of molecules of a hydroxyphenyl compound to a plurality of macromolecules of HA or collagen, to yield a plurality of macromolecules of HA or collagen including hydroxyphenyl groups, i.e. HPS-HA or HPS-C. The second step comprises cross-linking of a plurality of the hydroxyphenyl groups of HPS-HA and/or HPS-C to yield the cross-linked HPS-HA, cross-linked HPS-C, or both.

More specifically, in the first step, hydroxyphenyl groups are covalently-coupled to the macromolecules, periodically or randomly along the length of the macromolecules, via a carbodiimide-mediated reaction. In one embodiment, the covalent coupling can be accomplished between polycarboxylate macromolecules, or macromolecules that include carboxyl groups (or the cognate carboxylate groups, depending on pH), and molecules of a hydroxyphenyl compound that include a primary amine group. In another embodiment, the covalent coupling can be accomplished between polyamine macromolecules, or macromolecules including primary amine groups, and molecules of a hydroxyphenyl compound that includes a carboxyl group (or, again, the cognate carboxylate group, depending on pH). In either embodiment, the carbodiimide-mediated reaction catalyzes covalent coupling of the macromolecules and the molecules of the hydroxyphenyl compound through the carboxyl groups and primary amine groups.

In the second step, the hydroxyphenyl-substituted macromolecules are cross-linked via a dihydroxyphenyl bridge, i.e. a dihydroxyphenyl linking structure that is formed between hydroxyphenyl side groups on different macromolecules. Of note, some dihydroxyphenyl linking may also occur between different hydroxyphenyl side groups attached to the same macromolecule. In one embodiment, peroxidase in the presence of a dilute peroxide is able to extract the phenolic hydroxyl hydrogen atom from a hydroxyphenyl containing compound or side group, such as a tyramine side group, leaving the phenolic hydroxyl oxygen with a single unshared electron, an extremely reactive free radical. The free radical isomerizes to one of the two equivalent ortho-position carbons and then two such structures dimerize to form a covalent bond effectively cross-linking the structures, which after enolizing generates a dihydroxyphenyl dimer, e.g. a dihydroxyphenyl linkage such as a dityramine linkage. A suitable peroxide includes hydrogen peroxide ($H_2O_2$). A suitable peroxidase is horseradish peroxidase (also termed HRP). Alternatively, any other suitable enzyme or other agent can be used that is capable of generating free-radicals for cross-linking macromolecules that contain hydroxyphenyl side groups.

Considering the peroxidase enzyme in more detail, the peroxidase can either form hydroxyphenyl radicals required for cross-linking through interaction of hydroxyphenyl groups at the enzyme active site to directly create the desired radicals, or through generation of superoxide radicals, which then diffuse from the enzyme and interact with hydroxyphenyl groups to generate the desired radicals. Other compounds that have the potential to produce the same effect include any porphyrin containing compound, which includes the peroxidase family, hemoproteins, or the structurally related chlorin compounds. A number of other free radical initiators can also be used to crosslink the hydroxyphenyl-modified long-chain macromolecules, as previously described.

Hydroxyphenyl compounds that are suitable for the reaction include tyramine (also termed 4-(2-aminoethyl)phenol; 4-hydroxyphenethylamine; tyrosamine; 2-p-hydroxyphenylethylamine; p-β-aminoethylphenol; or α-(4-hydroxyphenyl)-β-aminoethane) and tyrosine (also termed L-tyrosine; Tyr; Y; β-(p-hydroxyphenyl)alanine; α-amino-p-hydroxyhydrocinnamic acid; (S)-α-amino-4-hydroxybenzenepropanoic acid).

Suitable HPS-HA can be formed by hydroxyphenyl substitution of hyaluronan, for example based on coupling of tyramine to 5% of the carboxyl groups of the glucuronic acid residues along the hyaluronan chain to form tyramine-substituted hyaluronan (also termed TS-HA), as previously described (e.g. U.S. Pat. No. 6,982,298). HPS-HA then can be cross-linked, e.g. by treatment with hydrogen peroxide (initiator) and peroxidase (catalyst), which causes neighboring hydroxyphenyl groups to form dihydroxyphenyl bridges, thereby cross-linking the HPS-HA, also as previously described with respect to TS-HA (e.g. U.S. Pat. No. 6,982, 298).

The HPS-HA can be made from HA of various molecular weights. HA is composed of repeating pairs of glucuronic acid (glcA) and N-acetylglucosamine (glcNAc) residues linked by a β1,3 glycosidic bond as shown in FIG. 1.

The glucuronic acid residue is particularly pertinent to the production of a HPS-HA as this sugar provides an available carboxyl group periodically along the repeat disaccharide structure of HA that is useful for hydroxyphenyl substitution, e.g. tyramine substitution. For each HA chain, this disaccharide can be repeated, for example, 2 to 10,000 or more times, resulting in a macromolecule that can have a molecular weight up to about 10 megadaltons. Adjacent disaccharide units of HA are linked by a β1,4 glycosidic bond, also as shown. Each glcA residue has a carboxylic acid group attached to the number 5 carbon atom of the sugar ring. Under biological conditions, HA is a negatively charged, randomly coiled polymer filling a volume more than 1,000 times greater than would be expected based on molecular weight and composition alone. The strong negative charges attract cations and water, allowing HA to assume the form of a strongly hydrated gel in vivo.

A suitable HPS-HA can be, for example, sterile, pharmaceutical grade TS-HA with a predetermined molecular weight and percent tyramine substitution, e.g. as manufactured in a GMP facility, and meeting various national and international quality and regulatory standards. Suitable TS-HA is available commercially, for example, from Lifecore Biomedical, Chaska, Minn.

Suitable HPS-C can be formed by hydroxyphenyl substitution of collagen, for example based on coupling of tyramine to 11% to 16% of the carboxyl groups of the aspartate and glutamate residues of collagen to form tyramine-substituted collagen (also termed TS-C), as previously described (1). HPS-C then can be cross-linked, e.g. again by treatment with hydrogen peroxide (initiator) and peroxidase (catalyst), also as previously described with respect to TS-C (1).

The HPS-C can be made from any of a wide variety of collagens. As used herein, the term collagen refers to a long, fibrous structural protein that is a major component of the extracellular matrix, which provides support to tissues and structure to cells. Collagen includes naturally occurring ("natural") collagens, such as type I, type II, type III, and type IV collagens, and engineered collagens, such as collagens available from FibroGen, Inc. (San Francisco, Calif.) and other commercial sources. Collagen also includes collagen in forms of any type, including single-stranded and multi-stranded collagenous proteins or polypeptides, the tropocollagen helix comprised of three polypeptide strands, such as type I collagen, and denatured-collagen products that substantially retain their native or engineered primary amino acid sequence. Such denatured-collagen products can be produced, for example, through hydrolysis or partial hydrolysis of the native or engineered fibrous collagen proteins, and include gelatin. Accordingly, modified or truncated collagenous proteins, such as gelatin, fall within the scope of collagen as used herein, as do more fibrous proteins, such as full length collagens. Collagen can be derived from any of various naturally-occurring sources, including humans and animals, and can be isolated and prepared according to conventional methods. Collagen can also be prepared or engineered synthetically based on amino acid and nucleic acid sequences for any of the various collagen types using conventional methods of molecular biology and protein expression. Likewise, gelatin can be produced from native or engineered collagens, or from denatured collagenous proteins, through conventional hydrolysis or other techniques as known in the art.

Suitable collagen includes, for example, type I collagen, type II collagen, type III collagen, type IV collagen, other native collagens, synthetic or engineered forms or types of collagen, highly purified recombinant collagen, collagen that is a component of a tissue extract, such as gelatin, and collagen that is a product of denaturation and hydrolysis of a naturally occurring, synthetic, or engineered collagen that substantially retains its primary amino-acid sequence, again such as gelatin. Regarding type I collagen in particular, suitable ranges of average molecular weight include, for example, 60,000-120,000 Daltons.

As noted, suitable collagen includes, for example, gelatin. As indicated above, gelatin is a partially hydrolyzed form of collagen. More specifically, gelatin is a heterogeneous mixture of water-soluble proteins of high average molecular weights, present in collagen, the proteins having been extracted from any one of various types of animals by boiling skin, tendon, ligaments, bones, and other organs in water. Gelatin is commercially available in various types, including type A, which is acid-cured gelatin, and type B, which is lime-cured gelatin. Gelatin can be produced from various animals, including pig (i.e. porcine gelatin), cow (i.e. bovine gelatin), and fish (i.e. gelatin from the skin of cold-water fish). Gelatin can be produced in various ranges of average molecular weights, including 20,000-25,000, 40,000-50,000, and 50,000-100,000 Daltons. Gelatin also can be produced having various Bloom values, including Bloom values of 100 to 300, 200 to 300, or 275 to 300. A suitable gelatin can be any of the various gelatins commercially available from Sigma-Aldrich Inc. (St. Louis, Mo.). Thus, for example, the HPS-C can be tyramine-substituted gelatin (also termed TS-G) made from type A porcine gelatin 300 Bloom, which is available commercially from Sigma-Aldrich, St. Louis, Mo.

Thus, in some examples, the cross-linked HPS-HA comprises cross-linked tyramine-substituted hyaluronan (TS-HA), the cross-linked TS-HA having been formed by cross-linking of tyramine groups of TS-HA to form dityramine bridges. Also, in some examples, the cross-linked HPS-C comprises cross-linked tyramine-substituted collagen (TS- C), the cross-linked TS-C having been formed by cross-linking of tyramine groups of TS-C to form dityramine bridges.

Considering the cross-linked HPS-HA and cross-linked HPS-C in more detail, the HPS-HA from which the cross-linked HPS-HA was formed can have had a weight average molecular weight of, for example, 0.1 MDa to 10 MDa, 0.5 MDa to 5 MDa, or 0.9 MDa to 1 MDa before having been cross-linked. The HPS-C from which the cross-linked HPS-C was formed can have had a Bloom value of, for example, 100 to 300, 200 to 300, or 275 to 300 before having been cross-linked. The HPS-HA from which the cross-linked HPS-HA was formed can have had a degree of hydroxyphenyl substitution of, for example, 0.5% to 15%, 1% to 10%, or 4% to 6% with respect to carboxyl groups of glucuronic acid residues of HA before having been cross-linked. The HPS-C from which the cross-linked HPS-C was formed can have had a degree of hydroxyphenyl substitution of, for example, 4% to 30%, 8% to 20%, or 11% to 16% calculated as moles of hydroxyphenyl groups per total moles of aspartate and glutamate of gelatin before having been cross-linked. The cross-linked HPS-HA, HPS-C, or both can have been cross-linked by treatment with horseradish peroxidase at a concentration, as provided, of, for example, 1 mU/µl to 20 mU/µl, 5 mU/µl to 15 mU/µl, 9 mU/µl to 11 mU/µl, or about 10 mU/µl, and hydrogen peroxide at a concentration, as provided, of, for example, 0.03% to 3%, 0.1% to 1.5%, 0.2% to 0.7%, or about 0.3%. The molecular weight or Bloom value, degree of hydroxyphenyl substitution, and extent of cross-linking affect the rates at which the cross-linked HPS-HA and/or cross-linked HPS-C are absorbed in vivo and thus can be controlled and/or modified in order to tune properties of the hydrogel of the coating.

Thus, in some examples, (i) the cross-linked HPS-HA comprises cross-linked TS-HA, the cross-linked TS-HA having been formed by cross-linking of tyramine groups of TS-HA to form dityramine bridges; (ii) the TS-HA from which the cross-linked TS-HA was formed having had a weight average molecular weight of 0.1 MDa to 10 MDa, 0.5 MDa to 5 MDa, or 0.9 MDa to 1 MDa before having been cross-linked; (iii) the TS-HA from which the cross-linked TS-HA was formed having had a degree of tyramine substitution of 0.5% to 15%, 1% to 10%, or 4% to 6% with respect to carboxyl groups of glucuronic acid residues of HA before having been cross-linked; and (iv) the cross-linked TS-HA having been cross-linked by treatment with horseradish peroxidase at a concentration, as provided, of 1 mU/µl to 20 mU/µl, 5 mU/µl to 15 mU/µl, 9 mU/µl to 11 mU/µl, or about 10 mU/µl, and hydrogen peroxide at a concentration, as provided, of 0.03% to 3%, 0.1% to 1.5%, or 0.2% to 0.7%, or about 0.3%. Also, in some examples, (i) the cross-linked HPS-C comprises cross-linked TS-C, the cross-linked TS-C having been formed by cross-linking of tyramine groups of TS-C to form dityramine bridges; (ii) the TS-C from which the cross-linked TS-C was formed having had a Bloom value of 100 to 300, 200 to 300, or 275 to 300 before having been cross-linked; (iii) the TS-C from which the cross-linked TS-C was formed having had a degree of tyramine substitution of 4% to 30%, 8% to 20%, or 11% to 16% calculated as moles of tyramine groups per total moles of aspartate and glutamate of collagen before having been cross-linked; and (iv) the cross-linked TS-HC having been cross-linked by treatment with horseradish peroxidase at a concentration, as provided, of 1 mU/µl to 20 mU/µl, 5 mU/µl to 15 mU/µl, 9 mU/µl to 11 mU/µl, or about 10 mU/µl, and hydrogen peroxide at a concentration, as provided, of 0.03% to 3%, 0.1% to 1.5%, or 0.2% to 0.7%, or about 0.3%.

The coating is immobilized on the bulk graft at the first surface of the bulk graft. The coating can be immobilized on the bulk graft at the first surface via the cross-linked HPS-HA, cross-linked HPS-C, or both. For example, the immobilization can be based on cross-linking of some of the hydroxyphenyl groups of HPS-HA, HPS-C, or both to amino acid residues, e.g. tyrosine residues, that may be present at the first surface of the bulk graft, e.g. for a bulk graft of which the biologic material or biologic-synthetic composite material comprises at least one of human extracellular matrix material, human acellular dermis matrix, non-reinforced human acellular dermis matrix, or reinforced human acellular dermis matrix, each of which include amino acid residues as a component of proteins thereof. Also for example, the immobilization can be based on HPS-HA, HPS-C, or both permeating a porous region of the biologic material or biologic-synthetic composite material of the bulk implant at the first surface, followed by cross-linking of hydroxyphenyl groups of the HPS-HA, HPS-C, or both, thus interlocking the cross-linked HPS-HA, cross-linked HPS-C, or both and the biologic material or biologic-synthetic composite material of the bulk implant at the first surface.

As will be appreciated, because the coating can be immobilized on the bulk graft at the first surface via the cross-linked HPS-HA, cross-linked HPS-C, or both, the immobilization can be carried out without relying on other approaches for immobilization. Thus, for example, the coating can be immobilized on the bulk graft at the first surface without carboxymethylcellulose immobilization.

As also will be appreciated, because the coating can be immobilized on the bulk graft at the first surface based on cross-linking of some of the hydroxyphenyl groups of HPS-HA, HPS-C, or both to amino acid residues that may be present at the first surface and/or based on interlocking the cross-linked HPS-HA, cross-linked HPS-C, or both and the biologic material or biologic-synthetic composite material of the bulk implant at the first surface, the immobilization can be carried out without the HPS-HA, HPS-C, or both permeating the biologic material or biologic-synthetic composite material of the bulk implant beyond a porous region of the first surface thereof. Thus, for example, the coating can be immobilized on the bulk graft at the first surface without the hydrogel substantially permeating the bulk graft below the first surface. For example, the coating can be immobilized on the bulk graft at the first surface such that the ratio of hydrogel below the first surface versus total hydrogel is less than 10%, less than 1%, less than 0.1%, or less than 0.01%. Also for example, the coating can be immobilized on the bulk graft at the first surface without the hydrogel being immobilized within the bulk graft.

The coating can have a thickness that is tailored depending on, among other things, whether the hydrogel of the coating comprises cross-linked HPS-HA, cross-linked HPS-C, or both. For example, the coating can have a thickness of 10 µm to 500 µm, 20 µm to 400 µm, or 40 µm to 200 µm, among other thicknesses. Also for example, for a hydrogel that comprises cross-linked HPS-HA, the coating can have a thickness of 10 µm to 500 µm, 100 µm to 250 µm, 150 µm to 200 µm, or approximately 175 µm, among other thicknesses. Also for example, for a hydrogel that comprises cross-linked HPS-HA, the coating can have a thickness of 100 µm to 200 µm, 125 µm to 175 µm, 140 µm to 160 µm, or approximately 150 µm, among other thicknesses. Also for example, for a hydrogel that comprises cross-linked HPS-C, the coating can have a thickness of 10 µm to 500 µm, 75 µm to 225 µm, 125 µm to 175 µm, or approximately 150 µm, among other thicknesses. Also for example, for a hydrogel that comprises cross-linked HPS-C, the coating can have a thickness of 20 µm to 100 µm, 30 µm to 80 µm, 40 µm to 60 µm, or approximately 50 µm, among other thicknesses.

Considering the bulk graft again, the bulk graft can further have at least a second surface. The second surface can be, for example, a second major surface of the bulk graft, again for a bulk graft having a flat, elongated form. Also, the second surface can be, for example, uncoated or coated. In addition, the second surface can be positioned, for example, opposite the first surface. Thus, in some examples, the bulk graft further has at least a second surface, the second surface being uncoated. Moreover, in some aspects of these examples, the second surface is positioned opposite the first surface. Also, in some examples, the bulk graft further has at least a second surface, the coating also being immobilized on the bulk graft at the second surface. Moreover, in some aspects of these examples, the second surface is positioned opposite the first surface.

The biocompatible tissue graft can be engineered to provide desired rates of bulk graft resorption and/or coating persistence based, for example, on the degree of hydroxyphenyl substitution and extent of cross-linking of the HPS-HA and/or HPS-C. Without wishing to be bound by theory, it is believed that cross-linked HPS-HA hydrogel coatings create a barrier against cellular infiltration from the juxtaposed mesenchymal tissue sources, whereas cross-linked HPS-C hydrogel coatings are permissive to cellular infiltration from such sources. It also is believed that use of HPS-HA and HPS-C having a suitable degree of hydroxyphenyl substitution, e.g. tyramine substitution, provides an advantage in terms of intermolecular cross-linking that is sufficiently high for formation of hydrogel coatings thereof but sufficiently low to allow most of the cross-linked HPS-HA and HPS-C to substantially maintain a native conformation and structural integrity. Thus, in some examples, the hydrogel comprises cross-linked HPS-HA, and the biocompatible tissue graft exhibits at least one of (i) bulk graft resorption of 24% or less, e.g. 20% or less or 15% or less, at 8 weeks following implantation thereof in a subject; or (ii) coating persistence of 50% or more, e.g. 70% or more or 90% or more, at 8 weeks following implantation thereof in a subject. Also, in some examples, the hydrogel comprises cross-linked HPS-C, and the biocompatible tissue graft exhibits at least one of (i) bulk graft resorption of 25% or more, e.g. 50% or more or 80% or more, by 8 weeks following implantation thereof in a subject; or (ii) coating persistence of less than 50%, e.g. less than 30% or less than 10%, by 8 weeks following implantation thereof in a subject.

The biocompatible tissue graft can be made as described in the Examples below, among other ways.

Also as noted above, in another example aspect, a method of repair of tissue damage in a subject in need thereof is provided. The method comprises surgically implanting a biocompatible tissue graft into a site of the tissue damage in the subject. The biocompatible tissue graft is as described above. Accordingly, the biocompatible tissue graft comprises a bulk graft. The bulk graft comprises a biocompatible material and has at least a first surface. The biocompatible tissue graft also comprises a coating. The coating comprises a hydrogel and is immobilized on the bulk graft at the first surface. The biocompatible material comprises at least one of a biologic material or a biologic-synthetic composite material. The hydrogel comprises cross-linked HPS-HA, cross-linked HPS-C, or both, the cross-linked HPS-HA, cross-linked HPS-C, or both having been formed by cross-linking of hydroxyphenyl groups of HPS-HA, HPS-C, or both to form dihydroxyphenyl bridges. Moreover, each of the examples and aspects of the biocompatible tissue graft as described above can be used with respect to the method.

The tissue damage can comprise, for example, a hernia, a ventral abdominal wall hernia, a rotator cuff injury, a pelvic organ prolapse, or a uro-gynecological injury. The site of the tissue damage can be, for example, a soft tissue, a mesenchymal tissue, an intraperitoneal tissue, a rotator cuff tissue, a pelvic tissue, or a uro-gynecological tissue. The intraperitoneal tissue can be, for example, a ventral abdominal wall tissue. The rotator cuff tissue can be, for example, a rotator cuff tendon. The pelvic tissue can be, for example, a bladder tissue. The uro-gynecological tissue can be, for example, a urethral tissue. Thus, for example, the method can comprise surgically implanting the biocompatible tissue graft, e.g. a hernia repair graft, into a site, e.g. an intraperitoneal tissue, such as a ventral abdominal wall tissue, of a hernia, e.g. a ventral abdominal wall hernia, in the subject. Also for example, the method can comprise surgically implanting the biocompatible tissue graft, e.g. a rotator cuff repair graft, into a site, e.g. a rotator cuff tissue, such as a rotator cuff tendon, of a rotator cuff injury in the subject. Also for example, the method can comprise surgically implanting the biocompatible tissue graft, e.g. a pelvic organ prolapse repair graft, into a site, e.g. a pelvic tissue, such as a bladder tissue, of a pelvic organ prolapse in the subject. Also for example, the method can comprise surgically implanting the biocompatible tissue graft, e.g. a uro-gynecological reconstruction graft, into a site, e.g. a uro-gynecological tissue, such as a urethral tissue, of a uro-gynecological injury in the subject.

In some examples, the site of the tissue damage comprises a tissue surface, and the implanting comprises positioning the biocompatible tissue graft in contact with the tissue surface. Also in some examples, the site of the tissue damage comprises a visceral tissue surface, and the implanting comprises positioning the coating of the biocompatible tissue graft in contact with the visceral tissue surface.

The Examples that follow are given by way of illustration only, not by way of limitation.

EXAMPLES

Example 1

The objective of this study was to identify a method for selectively coating the epidermal surface of HADM with a TS-HA hydrogel layer. Four 2×2 cm pieces of HADM (DermaMatrix, Musculoskeletal Transplant Foundation, Edison, N.J.) were rehydrated by pipetting 500 µl of 1% TS-HA (0.9-1 MDa MW with 5% tyramine substitution, Lifecore Biomedical, Chaska, Minn.)±10 mM HRP on their epidermal surface according to TABLE 1. After drying at room temperature overnight, all samples were treated with 500 µl 10 mM $H_2O_2$ to facilitate crosslinking in the HRP-treated samples. After curing at room temperature for an additional 4 hours, the samples were washed in ultrapure water for 10 minutes followed by a second overnight wash in ultrapure water. Untreated HADM was included as a control. For biochemical analysis, one 2×2 piece from each group was quartered and HA content was quantified in each sub-sample using the uronic acid assay. The second piece from each group was cryo-sectioned and HA localization was evaluated using HA binding protein (HABP) and hematoxylin and eosin (H&E) staining. The thickness of the TS-HA layer was measured across the epidermal surface on the H&E stained sections.

TABLE 1

TS-HA content and layer thickness on HADM

| HADM Treatment Groups (n = 2 per group) | TS-HA content (µg/mg) | TS-HA layer thickness (µm) |
|---|---|---|
| Untreated | 1.6 ± 0.1 | NA |
| 1% TS-HA in $H_2O$ + 10 mM $H_2O_2$ | 11.5 ± 3.1 | Not detected |
| 1% TS-HA in $H_2O$ + 10 U/ml HRP + 10 mM $H_2O_2$ | 25.3 ± 8.2 | 18.8 ± 11.5 |

Figure 2:
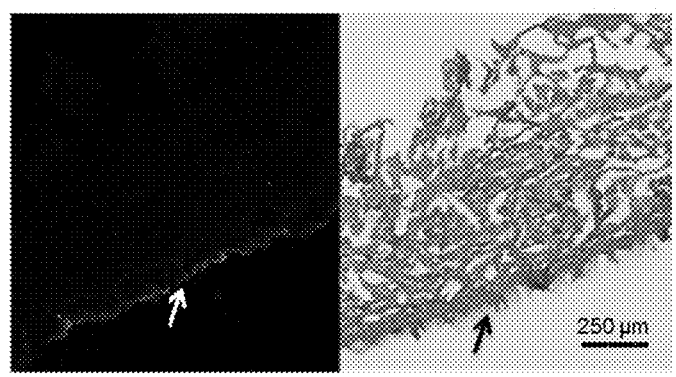
FIG. 2 shows a histologic section of HADM with TS-HA hydrogel layer (arrows) on epidermal surface. HABP (left) and H&E (right) staining (10×). Scale bar represents 250 µm.

Results: HADM coated with TS-HA+HRP+$H_2O_2$ had a ~20 µm hydrogel surface layer (TABLE 1), which was readily visualized on the histologic sections (FIG. 2, arrows). This study demonstrates that a TS-HA hydrogel layer can be selectively immobilized on the epidermal surface of HADM.

Example 2

Specific Aim 1: Investigate the cell and remodeling fate of human acellular dermis matrix (HADM) as a function of its juxtaposition and permissiveness to various mesenchymal tissues in a porcine screening model.

2.1 Introduction

Our approach will utilize (i) two implantation locations to juxtapose the HADM graft to different mesenchymal tissues, and (ii) two hydrogel coatings to modulate the HADM graft's permissiveness to cellular infiltration from these tissues. Specifically, we will investigate the cell and remodeling fate of HADM samples coated with gelatin or hyaluronan coatings on none, one, or both sides in intraperitoneal and retrorectus positions, in a porcine screening model. One of our working hypotheses is that permitting and/or preventing cellular infiltration from certain mesenchymal tissues leads to a "successful" graft, whereas permitting and/or preventing infiltration from other tissues leads to a "failed" graft (definition provided in 2.4.4). Our rationale for conducting these studies is that the influence of local tissue environment on graft fate is not well-characterized, an understanding of which is necessary for designing strategies to improve graft durability and reduce the incidence of complications and reherniation following ventral hernia repair (VHR). At the completion of these studies, we expect to understand how graft juxtaposition and permissiveness to various mesenchymal tissues influence its cell and remodeling fate, and define cell and vascular mechanisms of premature graft resorption. In so doing, we will also identify coating strategies which could be used to direct successful graft outcomes in proximity to specific mesenchymal tissues relevant to VHR.

2.2 Justification & Feasibility 2.2.1 Poor Long-Term Durability of Biologic Grafts Limits Successful Use in Ventral Hernia Repair Biologic grafts are recommended for VHR patients with bacterial contamination or high risk wounds, with such patients reported to represent as many as half of all hernia repairs. Biologic grafts are currently the preferred choice for laparoscopic intraperitoneal repair of hernias. In open repairs, placement of the biologic grafts in the retromuscular retrorectus space has become the standard procedure providing the best clinical results. Biologic grafts have the ability to be infiltrated with host cells and vascularized, and undergo a dynamic process of tissue remodeling. The ideal biologic graft should undergo constructive remodeling during which the rate of extracellular matrix (ECM) deposition exceeds graft resorption, or only partial remodeling with engraftment, such that the graft always possesses sufficient strength and integrity during healing. HADM grafts have initial mechanical properties that are similar to the abdominal wall. However, HADM grafts are known to possess inherent variability and often demonstrate poor long-term durability, resulting in repair bulging, dehiscence and reherniation. These data suggest that HADM grafts remodel too rapidly and/or too extensively to maintain their durability. Hence, research continues toward developing improved biologic graft materials that are biocompatible, resistant to infection, and mechanically durable. No commercially available graft meets all of these criteria, and there remains a critical need for new grafts that possess both adequate biologic and mechanical properties.

2.2.2 Graft Cellular Infiltration Influences Long-Term Durability

Clinical and preclinical studies show that biologic grafts used in VHR demonstrate a wide spectrum of host cell response and cellular graft infiltration. The anatomic location of graft placement clearly appears to influence graft cellularity and remodeling. For example, onlay, inlay or underlay repair techniques—which involve placing the graft over, within or underneath the hernia defect—are associated with different cellular characteristics in the graft. Similarly within underlay repairs, retrorectus placement of graft between muscle and fascia is associated with higher vascularity, remodeling, collagen deposition and graft integration compared to intraperitoneal placement where the graft interfaces only with peritoneal tissues. The omental peritoneum has a mesenchymal cell population that is pluripotent and angiogenic, and capable of differentiating into either fibrocollagenous tissues or vascularized adipose tissue, depending on the local in vivo environment. Hence, the specific mesenchymal host tissue adjacent to the graft appears to play an important role in determining graft cell and remodeling fate, but this relationship is not yet well-understood. By juxtaposing the graft to various mesenchymal tissues, and modulating the permissiveness of the graft interface to cellular infiltration, we aim to identify the cellular mechanisms associated with a loss of graft durability.

2.2.3 Hyaluronan Coating as Barrier to Cell Infiltration

Figure 3:
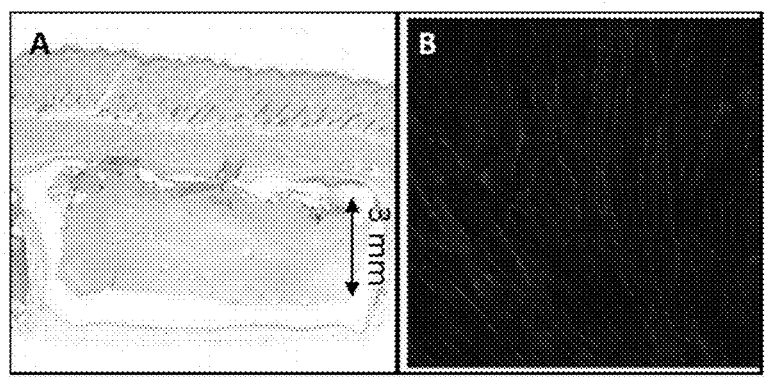
FIG. 3 shows (A) a subcutaneously implanted TS-HA plug and (B) a TS-G scaffold. (A) Subcutaneously implanted TS-HA plugs maintained their structure and shape after 12 months (rat). Scale bar represents 3 mm. (B) TS-G scaffolds (red) support cell (blue) proliferation and migration in vitro.

Hyaluronan, also termed hyaluronic acid or HA, is a naturally occurring glycosaminoglycan molecule in the ECM, where it plays a key role in several structural and biologic processes. It is non-immunogenic, non-toxic and non-inflammatory. HA has been used in solution, gel and membrane forms to coat hernia grafts to prevent the formation of peritoneal adhesions (2). We have developed tyramine-substituted hyaluronan (TS-HA), which has tyramine groups coupled to 5% of the carboxyl groups of the glucuronic acid residues along the HA chain (3). In the presence of hydrogen peroxide (initiator) and peroxidase (catalyst), neighboring tyramine groups cross-link to form dityramine bridges. TS-HA has been shown to be non-cytotoxic and biocompatible with suspended cells remaining metabolically active in the hydrogel (3). TS-HA hydrogel is not susceptible to hydrolysis, and in vivo degradation requires cellular internalization and depolymerization by lysosomal hyaluronidases. The absence of hyaluronidases in extracellular spaces results in very slow degradation kinetics of implanted TS-HA hydrogels. Subcutaneously implanted TS-HA hydrogel plugs with varying HA concentrations (6.25 to 100 mg/ml) showed biologic stability over 12 months post-implantation in rats, while maintaining structure and shape (FIG. 3 (A)). Further, the hydrogels resisted cellular invasion, and elicited a minimal inflammatory and fibrotic response.

2.2.4 Gelatin Coating as Permissive to Cell Infiltration

Gelatin is a heterogeneous mixture of partially-degraded ECM proteins, predominantly Type I collagen, and has been commonly used as a coating to improve cell attachment to substrates. Hydrogels composed of ECM degradation products have been shown to promote a constructive remodeling response in vivo, suggesting that ECM fragments may directly affect the default injury response.

Like TS-HA, we have developed a novel tyramine-substituted gelatin (TS-G) biomaterial (1) that retains the physiologic activity of gelatin and can form stable dityramine cross-linked hydrogels whose physical properties depend on concentration (4, 5). We have shown that TS-G hydrogel is recognized and bound by cells like native gelatin (1) (FIG. 3 (B)). Unlike native gelatin, TS-G does not melt at physiologic temperatures (37° C.), but like native gelatin, is readily degraded through proteases abundant in the ECM. Based on the overall promise of HA as a cell-barrier and gelatin as a cell-attractant, we propose herein to selectively coat the surface of HADM grafts with these biomaterials to create a barrier against (TS-HA), or make the graft permissive to (TS-G), cellular infiltration from the juxtaposed mesenchymal tissue sources.

2.2.5 TS-HA and TS-G Coating of HADM

We coated the epidermal surface of HADM grafts (DermaMatrix™, Musculoskeletal Transplant Foundation) with cross-linked TS-HA or TS-G. Briefly, a 500 µl solution with 10 mU/µl horseradish peroxidase and either 10 mg/ml TS-HA (0.9-1 MDa MW with 5% tyramine substitution, LifeCore Biomedical, Chaska, Minn.) or 50 mg/ml TS-G (derived from type A gelatin, 300 Bloom, Sigma-Aldrich) was pipetted on the epidermal surface of lyophilized 2×2 cm HADM grafts. This rehydration method effectively concentrated the macromolecular TS-HA or TS-G on the graft surface. The hydrogel coatings were cross-linked by air-drying overnight, rehydration in 0.03% hydrogen peroxide, followed by air-drying overnight. Samples were washed in ultrapure water for 10 minutes followed by a second overnight wash in ultrapure water.

Figure 4:
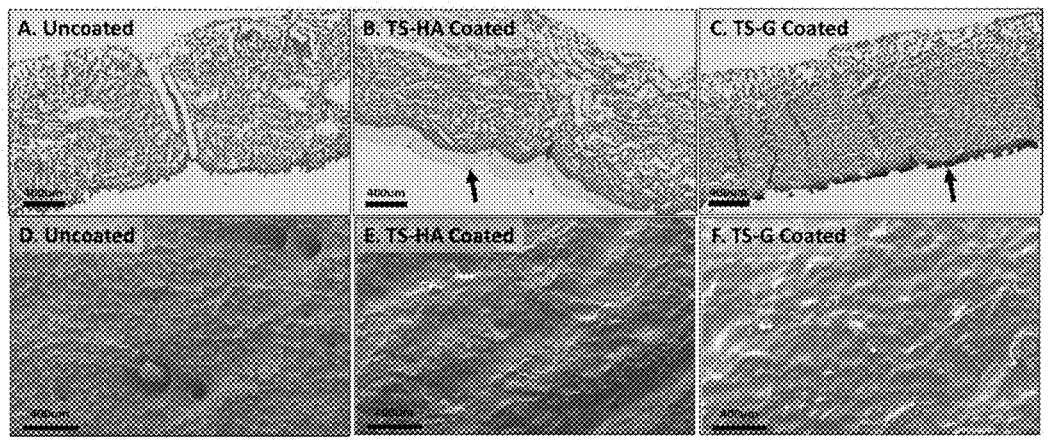
FIG. 4 shows H&E and scanning electron microscopy images of HADM. Representative H&E and scanning electron microscopy images show HADM (A, D) inherently contains surface irregularities, pores and holes from hair shafts. These features were masked after coated with either TS-HA (B arrow, E) or TS-G (C arrow, F). Scale bar represents 400 µm.

Histological evaluation of hematoxylin and eosin (H&E) stained grafts showed 150 µm thick TS-HA and 50 µm thick TS-G layers on only the coated epidermal surface of the grafts (FIGS. 4 (B) and (C), arrows). The TS-HA layer was thicker than TS-G, despite a lower starting concentration, due to electro-repulsive and osmotic effects for HA, not present for gelatin. Scanning electron microscopy confirmed the uniform nature of the TS-HA and TS-G coatings on the graft surface (FIGS. 4 (E) and (F)). Notably, the surface irregularities, pores and holes that were observed on the HADM surface (FIG. 4 (D)) were masked by the TS-HA and TS-G coatings. This study showed our ability to selectively, uniformly, and efficiently coat thin layers of TS-HA or TS-G on the surface of HADM grafts.

2.2.6 TS-HA and TS-G Coatings Influence Graft Function of HADM in Intraperitoneal Rat Model at 8 Weeks HADM grafts (2×2 cm) were coated with either TS-HA (cell-barrier) or TS-G (cell-attractant) on their epidermal surface. TS-HA coated, TS-G coated and uncoated HADM grafts (n=5/group) were implanted in a 1.2×1.2 cm full-thickness ventral hernia defect model in fifteen, male Sprague Dawley rats (retired breeders, >450 g, Harlan). HADM grafts were implanted in an intraperitoneal position with their coated-side facing the visceral peritoneum. The rats were euthanized at 8 weeks and evaluated for functional outcomes: hernia formation (defined as repair bulging under abdominal pressurization) and percent graft resorption (defined as a percent decrease in graft cross-sectional area), and cellular and vascular host response: severe foreign body reaction (defined as severe inflammation, encapsulation and fibrosis), neovascularization, and inflammatory and non-inflammatory cell infiltrate. All outcomes except hernia formation were assessed from H&E stained tissue sections at six step levels per sample as described in 2.4.3.

Figure 5:
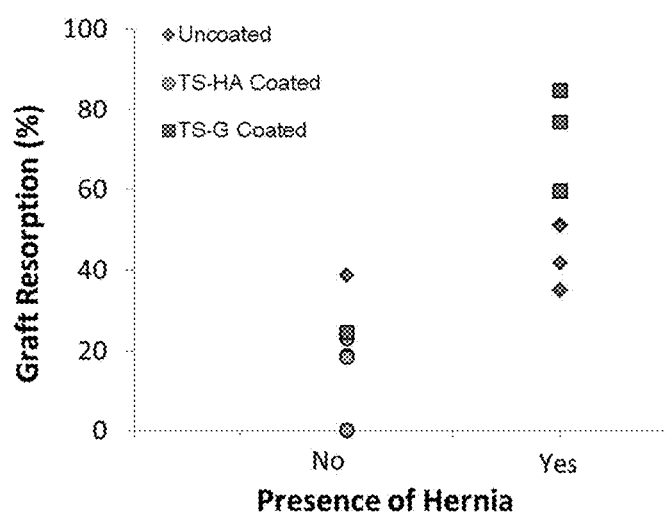
FIG. 5 is a plot of graft resorption (%) in the absence of hernia and the presence of hernia. The percentage of graft resorption is strongly and positively correlated with the presence of a hernia.

Results: One rat from the TS-G group was euthanized at 1 week for an unrelated complication (corneal ulcer). Graft resorption averaged 38±10% in the uncoated HADM group, with 3 of 5 repairs showing hernia formation (Table 2). Graft resorption averaged 12±11% in the TS-HA coated HADM group, with 0 of 5 repairs showing hernia formation. Graft resorption averaged 61±27% in the TS-G coated HADM group, with 3 of 4 repairs showing hernia formation. Across all groups, there was a strong positive correlation between the degree of graft resorption and the presence of a hernia (FIG. 5). Grafts with herniation (n=6) resorbed an average of 58±20% while grafts that did not herniate resorbed an average of 19±13% (n=8) at 8 weeks.

TABLE 2

Graft outcomes after 8 weeks implantation in a rat abdominal wall model (n = 5/group)

| Outcome | Uncoated | | | | | TS-HA Coated | | | | | TS-G Coated | | | | |
| --- | --- | --- | --- | --- | --- | --- | --- | --- | --- | --- | --- | --- | --- | --- | --- |
| | #1 | #2 | #3 | #4 | #5 | #1 | #2 | #3 | #4 | #5 | #1 | #2 | #3 | #4 | #5 |
| Hernia Formation | N | N | Y | Y | Y | N | N | N | N | N | — | Y | Y | N | Y |
| Graft Resorption (%) | 39 | 24 | 35 | 51 | 42 | 19 | 0 | 23 | 18 | 3 | — | 77 | 60 | 25 | 85 |
| Foreign Body Reaction | N | N | N | N | N | N | N | N | N | N | — | N | N | N | N |

Figure 6:
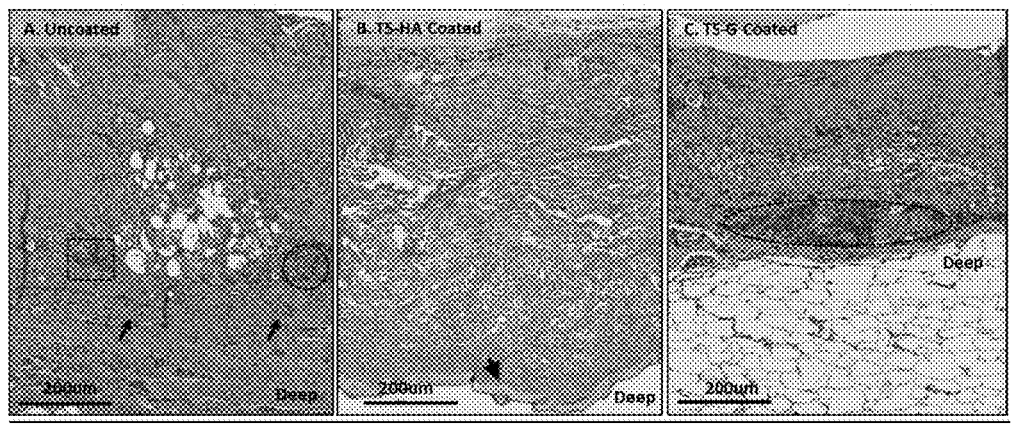
FIG. 6 shows cross-sections of HADM grafts at 8 weeks in the rat model. (A) An uncoated graft showing macrophages (circle), lymphocytes (rectangle) and neovascularization (arrow). (B) TS-HA coatings persist (arrow); non-inflammatory (fibroblast-like) cells were sparse in the deep and intermediate regions and abundant in the superficial region. (C) TS-G coatings were largely resorbed and an abundance of macrophages (ellipse) were observed near the deep surface. Scale bar represents 200 µm.

No evidence of severe foreign body reaction was observed for any repair graft. Repair grafts from all groups showed moderate neovascularization and focal aggregates of inflammatory cells consisting primarily of macrophages and lymphocytes (FIG. 6 (A)). Repair grafts from all groups showed a similar density of non-inflammatory cells (fibroblasts), which were uniformly distributed throughout the graft thickness in the uncoated and TS-G coated groups (FIGS. 6 (A) and (C)), but sparse in the deep and intermediate regions and abundant in the superficial region of the TS-HA coated grafts (FIG. 6 (B)). TS-HA coatings appeared to persist for 8 weeks (FIG. 6 (B)), and a thin fibrous tissue band was consistently observed spanning the deep surface of the TS-HA grafts though not adhered to it. In contrast, the TS-G coatings were largely resorbed at 8 weeks and an abundance of macrophages were observed near the deep surface of the TS-G grafts (FIG. 6 (C)).

Conclusions: TS-HA coating of HADM persisted for 8 weeks and was associated with only sparse cellular infiltration on the coated side, limited graft resorption and no occurrence of hernias. These data suggest that TS-HA acted like a barrier to cellular infiltration. Whereas TS-G coating of HADM was associated with uniform cellularity, extensive graft resorption and a 75% likelihood of hernia formation, suggesting TS-G acted as a cell-attractant. Collectively, these outcomes support our rationale for using TS-G and TS-HA coatings to consistently present HADM to adjacent mesenchymal tissues as permissive or non-permissive to cellular infiltration and as a possible strategy to improve biologic graft durability after implantation. In general TS-G and TS-HA coatings had distinctive and opposite effects on graft resorption compared to uncoated HADM. Since the cross-linking chemistry was identical for both coatings, this suggests that functional graft outcome was independent of the cross-linking chemistry utilized. Finally, there was a strong positive correlation between the degree of graft resorption and the presence of a hernia in this study, suggesting graft resorption can be used as functional surrogate in the proposed porcine screening model.

Figure 7:
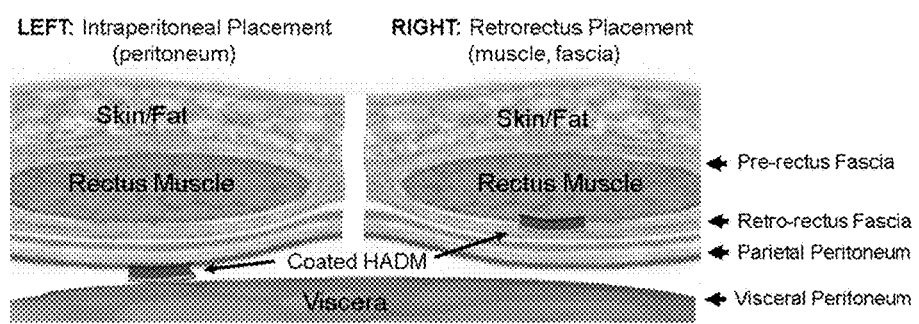
FIG. 7 illustrates positioning of coated HADM in accordance with intraperitoneal placement (left) and retrorectus placement (right). Each pig will receive five 1.5×1.5 cm HADM implants in the intraperitoneal location on the left side and five HADM implants in the retrorectus location on the right side of their midline.

2.2.7 Porcine Screening Model to Study Graft Cellular Infiltration in Intraperitoneal and Retrorectus Locations The ventral abdominal wall anatomy of the rat permits graft placement in intraperitoneal (2.2.6), but not the retrorectus location. However, both implantation locations are highly relevant to VHR-laparoscopic intraperitoneal repair and open retrorectus repair are currently the preferred VHR procedures providing the best clinical results. The two locations also constitute unique mesenchymal cell and tissue environments for the graft—the intraperitoneal location interfaces the graft against peritoneal tissues whereas the retrorectus location interfaces the graft against muscle and fascia (FIG. 7). The pig abdominal wall anatomy permits graft placement in both locations and also permits implantation of multiple implants in the same animal. Immune cell response is commonly investigated in transplant studies and vaccine development studies, where the pig is the model of choice and reagents are well-established. Based on the above rationale and our intent to use the pig as a ventral hernia repair model (2.2.2), we therefore propose to use the pig as a screening model to define the relationship between the graft's downstream cell and remodeling fate and its physical juxtaposition and permissiveness to cellular infiltration from various mesenchymal tissues.

2.3 Study Design Overview

Our approach will be to coat HADM samples with TS-HA and/or TS-G in order to consistently present HADM to adjacent tissues as either non-permissive (TS-HA coating) or permissive (TS-G coating) to cellular infiltration. Coated HADM samples (1.5×1.5 cm) will be implanted in both intraperitoneal and retrorectus positions in 32 pigs using a block design. Each pig will receive five implants in the intraperitoneal location on the left side and five implants in the retrorectus location on the right side of their midline (FIG. 7).

The design involves three sub-Aims. In Aim 1A we will evaluate HADM grafts coated with TS-HA or TS-G on one or both side(s) (8 experimental combinations) and a non-coated control (n=10/group/location), for the purpose of identifying at least 4 combinations in both intraperitoneal and retrorectus locations with ≥7% probability of a successful graft outcome (defined in 2.4.4) at 8 weeks. HADM grafts will be implanted in 18 pigs using a balanced incomplete block design, with grafts from 5 different groups represented in each animal and location. In Aim 1B, we will evaluate the 4 coating combinations considered successful in each location at 8 weeks and the non-coated control (n=10/group/location), for the purpose of identifying the 2 coating combinations in each location with the highest probability of a successful graft outcome (defined in 2.4.4) at 16 weeks. Grafts will be implanted in 10 pigs using a balanced complete block design, with grafts from all 5 groups represented in each animal and location. In Aim 1C, we will evaluate the 2 most successful coating combinations in 1B and 2 failed coating combinations associated with maximum graft resorption in 1A and the non-coated control at 2 and 4 weeks (n=4/group/time/location), for the purpose of defining cell and vascular outcomes associated with successful/failed grafts in each location. Grafts will be implanted in 4 pigs per time point using a balanced complete block design, with grafts from all 5 groups represented in each animal and location. At sacrifice in all sub-Aims, all implants will be retrieved and evaluated histologically for foreign body reaction, graft resorption, inflammatory and non-inflammatory cell infiltrate and vascularity.

Statements of Rationale: Non-coated HADM grafts will be included as a control in each sub-Aim because they represent the current clinical standard for hernia repair with a biologic graft. We have chosen 8 weeks for our initial down-select experiment based on evidence from our preliminary study (2.2.6) that the direction of graft fate will be largely evident by that time. A probability of success 7% was chosen to be "reasonably promising but not overly stringent" for down-selection experiments.

2.4 Detailed Methods 2.4.1 HADM Coatings

HADM grafts (1.5×1.5 cm) for all sub-Aims will be coated with TS-HA and/or TS-G according to 2.2.5. The thickness and length of each graft will be measured at 5 locations using a micrometer.

2.4.2 Porcine Biomaterials Screening Model (Intraperitoneal and Retrorectus Locations)

Pigs will be anesthetized, intubated and placed in the supine position. The abdomen will be shaved, scrubbed, prepped and sterile-draped. A 15-20 cm ventral midline skin incision will be made, and 1 cm skin flaps will be raised. A 15 cm full thickness incision will be made through the linea alba starting 6 cm caudal to the xiphoid process. Five HADM grafts will be implanted in each location (FIG. 7). Left side, intraperitoneal implantation: the grafts will be affixed to the parietal peritoneum, and the peritoneum and linea alba will then be closed using a continuous stitch of 2-0 PDS. Right side, retrorectus implantation: a 15 cm incision will be made along the medial edge of the anterior rectus sheath and the retrorectus space between the rectus abdominis muscle and the posterior rectus sheath will then be separated. The grafts will be affixed to the exposed surface of the posterior rectus sheath, and the incision on the anterior rectus sheath will be closed using a continuous stitch of 4-0 PDS. In each location HADM grafts will always be placed epidermal surface deep, affixed using 5-0 Prolene mattress sutures at their four corners, and distanced at least 1.5 cm apart over a 10×5 cm region. The midline skin incision will be closed in layers with 2-0 PDS and covered with an adhesive bandage.

Sample Recovery: At euthanasia the previous surgical incisions will be reopened to expose the intraperitoneal and retrorectus graft placement locations. Each graft will be removed en bloc for histologic analysis.

2.4.3 Outcomes

Grafts will be fixed and processed for routine paraffin embedding. Each graft will undergo step-level sectioning at 2 mm increments (yielding 6 step levels), capturing 10 sections at each level. One section at each level will be stained with H&E or immunostained according to TABLE 3.

All stained sections will be scanned in their entirety at 20× using a Leica SCN400F scanner (Leica Microsystems, GmbH, Wetzlar, Germany).

Severe Foreign Body Reaction: Each graft will be assessed for severe foreign body reaction from the H&E scanned section at each step level, defined as severe inflammation, encapsulation and fibrosis.

Graft Resorption: Graft resorption will be defined as the percent decrease in cross-sectional area from implantation to explantation. Graft cross-sectional area at implantation will be defined as its initial thickness times its length. Graft cross-sectional area at explantation will be defined by outlining and measuring the remaining graft area on the H&E scanned section from each step level using ImageScope (Version 12.0.1 Leica Microsystems Inc., Buffalo Grove, Ill.) and averaging these six measures.

Cell and Vascular Outcomes: Each graft will be quantitatively assessed for inflammatory cells (T- and B-lymphocytes, macrophages and their M1/M2 subpopulations), non-inflammatory cells, total cells and endothelial cells. Briefly, sections at each step level will undergo antigen retrieval followed by fluorescence immunostaining to identify cell types using antibodies as in TABLE 3. FITC-conjugated goat polyclonal anti-rabbit IgG (A120-201F, Bethyl Laboratories) and Cy3-conjugated goat anti-mouse IgG (A90-516C3, Bethyl Laboratories) secondary antibodies will be used. Sections will be counterstained with DAPI to identify all cell nuclei. After scanning, custom software will be used to manually outline the graft area on each section, and to count the number of $CD3^+$, $CD79a^+$, $CD68^+$, $CD68^+/iNOS^+$, $CD68^+/Arginase-1^+$ cells as well as the total cells ($DAPI^+$) within the graft area. Non-inflammatory cell number will be defined as the difference between total and all inflammatory cells in each section. The ratio of each cell type to total cells will be computed for each section, and a vascular area fraction will be computed from the ratio of area of $vWF^+$ cells to total graft area on each section. All outcomes will be averaged across the six step levels to represent a given graft sample.

TABLE 3

Primary antibodies for localization of inflammatory cells associated with coated and uncoated dermis: Abcam, Inc., Cambridge, MA; Santa Cruz Biotechnology, Santa Cruz, CA; Dako, Carpenteria, CA; Abnova, Taipei, Taiwan)

| Cell Type | Identifying Antigen(s) | Primary Antibody |
| --- | --- | --- |
| T-lymphocyte | $CD3^+$ | Rabbit monoclonal anti-CD3 (ab16669, Abcam) |
| B-lymphocyte | $CD79a^+$ | Mouse monoclonal anti-CD79a (ab3121, Abcam) |
| Pan Macrophage | $CD68^+$ | Mouse monoclonal anti-CD68 (MAB1715, Abnova) |
| M1 Macrophage | $CD68^+/iNOS^+$ | Rabbit polyclonal anti-iNOS (sc-8310, Santa Cruz) |
| M2 Macrophage | $CD68^+/Arginase-1^+$ | Rabbit polyclonal anti-Arginase-1 (sc-20150, Santa Cruz) |
| Endothelial Cell | $vWF^+$ | Rabbit polyclonal anti-Van Willebrand Factor (vWF) (A0082, Dako) |

2.4.4 Definition of a Successful Graft Outcome in Porcine Screening Model (Aim 1A and 1B)

Our preliminary study showed a strong correlation between graft resorption and hernia formation in the rat model (2.2.6). Based on the resorption data from grafts that did not experience hernia formation, the following two criteria will be used for triaging a successful graft outcome in our screening model: (1) no foreign body reaction and (2) ≤25% graft resorption.

2.5 Statistical Analysis

Statistical analysis and decision making will be performed independently for samples in the intraperitoneal and retrorectus locations:

2.5.1 Specific Aim 1A: Our objective is to identify all coating combinations in both locations with ≥70% probability of a successful cell and remodeling outcome at 8 weeks. There will be n=10 replicates per coating combination/location. The probability of success for each coating combination will be computed as the ratio of successful to total replicates. All coating combinations with at least 7 out of 10 successes in each location will be investigated in Aim 1B. We assumed that four coating combinations in each location will pass the criteria for successful outcome with ≥70% probability at 8 weeks.

2.5.2 Specific Aim 1B: There will again be n=10 replicates per coating combination and location, and the probability of success for each coating combination will be computed as the ratio of successful to total replicates. In this instance, we have not set a firm cut-off for probability of success because our objective is to identify the two coating combinations with highest probability of success at 16 weeks. We expect there will be at least two coating combinations at each location that will continue to show ≥70% probability of success (i.e., at least 7 successes out of 10 replicates) at 16 weeks.

2.5.3 Specific Aim 1C: The objective is to define the cell and vascular mechanisms associated with successful versus failed grafts in both the intraperitoneal and retrorectus locations. This will be accomplished by identifying differences in cell and vascular outcomes between successful and failed grafts at 2, 4, and 8 weeks. For each location and time, we will reduce the outcome data from five treatment groups to two analysis groups: successful and failed grafts. The successful group will include data from the two successful coating combinations, and the failed group from the two failed coating combinations and the non-coated control (which we expect to fail the criteria for successful outcomes at 8 and 16 weeks). Hence for each location, the successful group will have a sample size of n=8 at 2 and 4 weeks and n=20 at 8 weeks, and the failed group will have a sample size of n=12 at 2 and 4 weeks and n=30 at 8 weeks. We will use an unbalanced 2-way analysis of variance (ANOVA) (two groups, three time points) with custom contrast statements for pairwise comparisons between selected group means (within group or within time). Bonferroni corrections will be used to adjust for multiple comparisons. Any contrast with $p<0.05$ will be considered statistically significant.

2.6 Sample Size Justification 2.6.1 Specific Aims 1A and 1B: The power analysis for these two sub-aims was performed by assuming each coating combination started as a population of 100% successes and progressed to a population with some proportion of failures at 8 or 16 weeks. For a sample size of 10, we have power of 0.76, 0.60, and 0.44 to detect 50%, 60% and 70% probability of success respectively at alpha=0.05. Although the level of power for 70% probability of success (0.44) is less than the desired 0.8, we consider it sufficient to provide reasonable confidence for screening and down-selection purposes, while also utilizing a practical and achievable number of large animals (n=28 for these two sub-Aims). Furthermore, true validation of the grafts considered successful in this screening model will be assessed in a clinically relevant ventral hernia repair model, using a study designed with 0.80 power at alpha=0.05 (Specific Aim 2).

2.6.2 Specific Aim 1C: A sample size of 8 successful grafts and 12 failed grafts at 2 and 4 weeks and 20 successful and 30 failed grafts at 8 weeks will allow us to detect an overall effect size of 1 in any outcome within the ANOVA with power=0.8 and p=0.05, where effect size is the number of standard deviations the means differ by. For specific contrasts, these samples sizes will allow us to detect an effect size of 2 in any outcome at 2 and 4 weeks and an effect size of 1.2 in any outcome at 8 weeks with power=0.8 and p=0.05.

2.7 Expected Outcomes

We expect that completion of the full study design which investigates both coatings, together or separately, on one or both sides of the graft, and in two tissue environments will provide a broad understanding of HADM graft fate as a function of its juxtaposition and permissiveness to various mesenchymal tissues. At the conclusion of Specific Aim 1C we expect to identify differences in cell and vascular outcomes between successful and failed grafts at 2, 4 and 8 weeks. Significant findings from Specific Aim 1C will be used collectively to describe the cell and vascular mechanisms associated with successful graft outcomes.

Further, at the completion of Specific Aim 1 we expect to have identified at least 2 coating combinations (at each of the intraperitoneal and retrorectus locations) that will show ≥70% probability of success at 16 weeks, and chosen the best 2 at each location for investigation in Specific Aim 2. We do not expect that the same HADM coating combinations will necessarily prove to be most successful in both tissue locations, given the unique mesenchymal cell and tissue environment of the intraperitoneal and retrorectus spaces. For example, our preliminary data suggest we might expect that using a coating which prevents cellular infiltration from the visceral peritoneum will lead to a successful graft (limited resorption) in that location, whereas using a coating which consistently presents the graft as permissive to cellular infiltration will lead to a failed graft in that location (extensive resorption). However, the reverse may be true when juxtaposed to, for example, muscle.

Example 3

Specific Aim 2: Validate that select HADM coating combination(s) improve outcomes in pre-clinical porcine models of (2A) intraperitoneal and (2B) retrorectus ventral hernia repair.

3.1 Introduction

Our approach will evaluate HADM coated with select combinations of TS-HA and/or TS-G in the context of two pre-clinical models: intraperitoneal (Aim 2A) or retrorectus (Aim 2B) ventral hernia repair (VHR). Repairs with untreated HADM will be used as controls. For each VHR study, one of our working hypotheses is that repairs with selectively coated HADM will be clinically and functionally superior to repairs with untreated HADM. Our rationale for conducting these studies is that coating combinations yielding positive cell and remodeling outcomes in a given tissue environment (Aim 1) only infer a strategy for improving HADM performance in hernia repair, and would benefit from being validated in the context of VHR, at pre-clinical scale, and with assessment of clinical and functional outcomes. At the completion of these studies, we expect to identify up to 2 coating strategies for improving biologic graft durability leading to successful outcomes in the context of both intraperitoneal and retrorectus ventral hernia repair.

Figure 8:
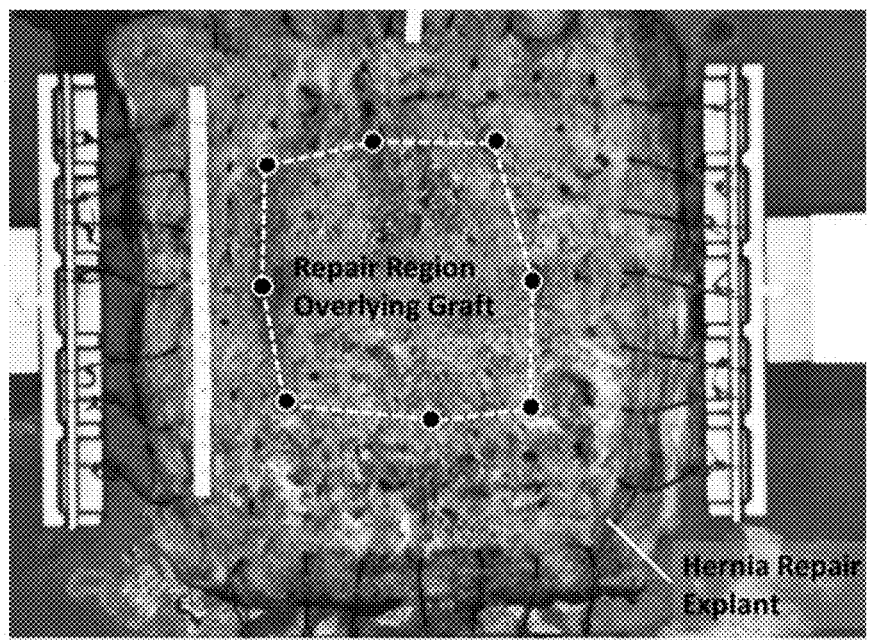
FIG. 8 shows planar biaxial mechanical test set up and preliminary results for tests of load to failure. (A) Planar biaxial mechanical test set-up with a 15×15 cm abdominal wall explant. The explant surface was marked to delineate and optically track the repair region. (B) Preliminary load to failure tests suggest that HADM repairs are compliant at time-zero, but gradually increase toward the native abdominal wall in strength and stiffness with increasing repair period.
Figure 8:
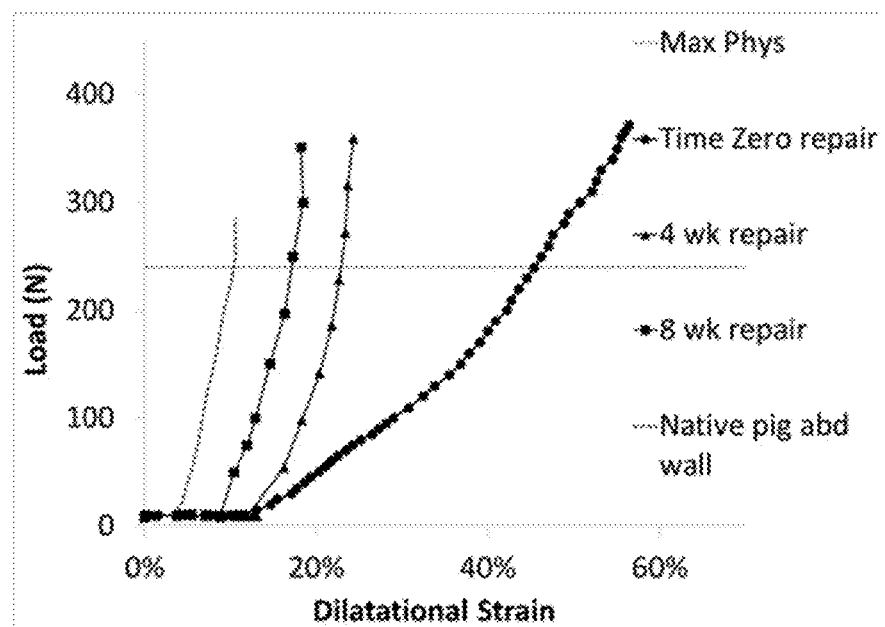

3.2 Justification & Feasibility 3.2.1 Ventral Hernia Repair in the Porcine Model We created a full-thickness, midline 8×8 cm ventral abdominal wall defect in two female Yorkshire pigs (~35 kg). The defects were repaired with a 12×12 cm HADM graft fixed in an intraperitoneal underlay technique using interrupted horizontal mattress sutures (2-0 Prolene) allowing 2 cm of underlap. We euthanized the pigs at 4 and 8 weeks post-surgery (n=1 per time point). Immediately prior to euthanasia, the pigs were administered systemic muscle relaxant (1 mg/kg vecuronium bromide, IV) to prevent post-mortem muscle contracture. 15×15 cm portions of the ventral abdominal wall inclusive of repair region were resected en bloc and mechanically tested within 2 h post-mortem. (Both post-mortem muscle contracture and rigor mortis can confound biomechanical test data). The explants were equibiaxially loaded to failure using an ADMET planar biaxial test apparatus (FIG. 8 (A)). The explant surface was marked to delineate and optically track strains in the repair area. Imaging data were analyzed using a quadratic quadrilateral element based finite element analysis (custom MATLAB script) to estimate average dilatational strains (percent increase in area) of the repair region. FIG. 8 (B) shows a plot of load versus dilatational strain of the repair area for the 4 and 8 week HADM repairs, two native abdominal wall explants and 6 time-zero HADM repairs. The time-zero repairs showed a % Dilatational Strain (DS) at 16 N/cm of 40±7%, and a Linear Stiffness of 785±86 N/% DS. These data suggest that HADM intraperitoneal underlay repairs are compliant at time-zero, but the linear stiffness gradually increased and percent dilatational strain at 16N/cm gradually decreased toward native abdominal wall with increasing repair period. These data also demonstrate our method for sophisticated biaxial mechanical testing of the entire repair construct.

3.2.2 Pre-Clinical Porcine Models of Intraperitoneal Underlay and Retrorectus Ventral Hernia Repair The pig is considered the most suitable large animal model for ventral hernia repair due to its anatomic and physiologic similarities to human (size and bulk of the ventral abdominal wall, cutaneous blood supply and wound healing characteristics). Functional outcomes such as hernia occurrence and end-point repair biomechanics (outcomes studied in Aim 2) are best studied in a large animal model like the pig that allows creation of critical-sized defects which can be repaired with grafts similar in size to grafts used in human patients. Furthermore, the pig model also allows both intraperitoneal and retrorectus graft placement. We have developed rigorous ventral hernia repair models of intraperitoneal and retrorectus repair and methods for biaxial mechanical testing of the abdominal wall explant in the pig model (3.2.1) and herein propose to use the pig ventral hernia repair models to validate the grafts considered successful in the screening model from Aim 1.

3.3 Study Design Overview

A total of 90 pigs will be used in Specific Aim 2. We will investigate the 2 coating combinations associated with the highest probability of a successful cell and remodeling outcome in juxtaposition to peritoneum in Aim 1, in a pre-clinical model of intraperitoneal VHR (Specific Aim 2A, n=30 pigs). Likewise, we will investigate the 2 coating combinations that conferred the highest probability of a successful cell and remodeling outcome in juxtaposition to muscle/fascia in Aim 1, in a pre-clinical model of retrorectus VHR (Specific Aim 2B, n=30 pigs). In both VHR models, untreated HADM will be included as control. Animals in both studies will be sacrificed at 16 weeks. All animals will be assessed for clinical evidence of hernia formation, followed by biomechanical testing and histologic analysis of the entire repair construct. Additional pigs will be obtained for determining the mechanical properties of time-zero controls: native porcine abdominal wall (n=10), intraperitoneal repair constructs (n=10) and retrorectus repair constructs (n=10).

Statements of Rationale: Non-coated HADM grafts will be included as controls because they represent the current clinical standard for hernia repair with a biologic graft. Furthermore, post-implantation remodeling of non-cross-linked dermis grafts is known to complete in 16-24 weeks and an endpoint of ~16 weeks is commonly used for pre-clinical studies in the porcine model. Hence, we propose to evaluate ventral hernia repair at 16 weeks. Finally, while the surgical models investigated herein do not represent the most challenging VHR conditions that are most prone to premature graft resorption clinically (e.g., infection, co-morbidities, etc.), the proposed studies will yield fundamental knowledge about how local mesenchymal tissue environment influences graft fate and ultimately VHR outcomes in clinically relevant scenarios and thus provide the foundation for future work addressing the more challenging scenarios of VHR.

3.4 Detailed Methods 3.4.1 HADM Coatings

HADM grafts (12×12 cm) will be coated with TS-HA or TS-G according to methods described in 2.2.5. We expect that some optimization for scaling up the coating procedures will be needed, e.g., using a double syringe-based delivery and coating device instead of a pipette.

3.4.2 Porcine Models of Ventral Hernia Repair

Pigs will be anesthetized and prepared for abdominal surgery according to 2.4.2. A 12 cm ventral midline skin incision will be made, and 1 cm skin flaps will be raised. Starting 10 cm caudal to the xiphoid process, a 10 cm full thickness incision will be made through the linea alba.

Intraperitoneal Repair (Aim 2A): A 12×12 cm HADM graft will be affixed to the parietal peritoneum in an underlay fashion with eight circumferential transfascial 2-0 Prolene sutures Transfascial sutures will be passed through abdominal wall musculofascia and button-hole skin incisions using a Reverdin needle.

Retrorectus Repair (Aim 2B): The midline incision in the linea alba and peritoneum will be immediately closed using a continuous stitch of 2-0 PDS. Then a 10 cm incision will be made bilaterally along the medial edge of the anterior rectus sheath. The retrorectus space between the rectus abdominis muscle and the posterior rectus sheath will be separated bilaterally by blunt dissection to create a 12×12 cm pocket centered on the midline. A 12×12 cm HADM graft will be positioned in the established retrorectus pocket and affixed to the overlying rectus muscle by transfascial sutures as above.

The incision in the linea alba will not be closed. Each button-hole skin incision will be closed with a single subcutaneous 4-0 PDS stitch. The midline skin incision will be closed as in 2.4.2.

Euthanasia and Sample Recovery: At 16 weeks, pigs will be administered systemic muscle relaxant (1 mg/kg vecuronium bromide, IV) to facilitate post-mortem mechanical testing of the surgical constructs, and then euthanized. 25×25 cm portions of the ventral abdominal wall inclusive of repair region will be resected en bloc for biomechanical and histologic analysis.

3.4.3 Outcomes

Hernia Formation: Bi-weekly, all pigs will be physically examined for clinical occurrence of hernia by a veterinarian.

Biomechanical Properties: Mechanical testing will be completed within 2 h post-mortem to avoid confounding influence from rigor mortis. Abdominal wall explants (and time zero controls) will be tested using planar biaxial tests and videometric strain analysis (3.2.1). The following parameters will be reported: Linear Stiffness, % Dilatational Strain at 16N/cm membrane tension, % Dilatational Strain at Failure, Membrane Tension at Failure, and Failure Load. The true membrane tension at the repair edge (N/cm) will be estimated from the ratio of the biaxial load per the instantaneous repair-edge length. Using a simplifying assumption that the repair region retains its original square shape, we will approximate the effective instantaneous graft-edge length as the square root of the area of the deformed repair region. A bilinear curve fit of the membrane tension and dilatational strain data will be used to obtain the linear stiffness of the repair (slope of the second linear region). The average dilatational strains in the repair region will be determined at biaxial loads of 240N (the estimated physiologic load of 16N/cm on 15×15 cm abdominal wall tissue). The membrane tension and dilatational strain at failure will be reported. Failure load, mode and location will also be recorded.

Descriptive Histology: After biomechanical testing, transverse tissue strips spanning the entire defect area will be dissected from the cranial, mid and caudal portions of the explant and processed for routine paraffin histology. One H&E stained section from each region will be descriptively reviewed for inflammatory and non-inflammatory cell types and vascularity.

3.5 Statistical Analysis

The intraperitoneal (Aim 2A) and retrorectus (Aim 2B) VHR studies will be analyzed independently, but the statistical methods for each are identical. For each study, our working hypothesis is that repairs with selectively coated HADM will be functionally superior to repairs with untreated HADM. Our primary outcomes for hypothesis testing are pre-failure repair biomechanics (linear stiffness and percent dilatational strain at 16N/cm). For each outcome there will be n=10 measures per group and three groups in each study. We will use ANOVA or non-parametric tests as appropriate, together with post-hoc testing, to examine whether one or both of the HADM coated groups yield biomechanically superior repairs compared to untreated HADM repairs. We will also test if repairs with one HADM coating combination are biomechanically superior to the other for a given type of repair. Finally, although not a primary research question, the repair groups yielding the best biomechanical outcomes for each surgical model will be compared using t-tests to identify whether the best-case intraperitoneal VHR is inferior/superior to the best-case retrorectus VHR. $p<0.05$ will be significant.

For each study, clinical hernia formation will be investigated as a secondary outcome; since it is not clear if these more severe functional deficits will manifest themselves in the proposed 16 week surgical models, they are not considered as a primary outcome. The histologic outcomes will be used as confirmatory of the expected limited graft resorption and non-inflammatory cellular response in successful repairs.

3.6 Sample Size Justification

No previous studies have used planar biaxial mechanical testing to characterize the sub-failure properties of the entire VHR construct. Few studies have tested the entire VHR construct in any manner, and those that have used burst testing and report only failure data. Most studies that report on the biomechanical properties of VHR used uniaxial tensile tests of a portion of the repair, and typically reported only failure data. Hence there is no directly appropriate data upon which to base the sample size estimation for the proposed studies. Consequently, we estimated the expected variance for our biomechanical outcomes from two sources: first our own preliminary data of the entire VHR repair construct at time zero, in a porcine model, repaired with HADM and tested in planar biaxial mode (n=6) showed the standard deviation was 18% of the mean for percent dilatational strain (DS) at 16 N/cm (40±7%) and 11% of the mean for stiffness (785±86 N/% DS). Second, literature data of a portion of VHR repair constructs at one to six months post-implantation, in various porcine models, repaired with human or porcine dermis, and tested in uniaxial tension, reported standard deviations 10-36% of the mean for biomechanical parameters. Based on these data collectively, we will assume pooled standard deviations of 20% for our biomechanical outcomes in the proposed studies. We powered our study to detect a mean increase of 30% in linear stiffness and/or decrease of 30% in DS at 16N/cm in repairs with coated HADM compared to repairs with untreated HADM, based on the rationale that a 30% improvement in repair function would be clinically important. A sample size of ten/group (3 groups) will allow us to detect an effect size of 30/20=1.5 with power=0.8 and p=0.05.

3.7 Expected Outcomes

At the completion of these studies, we expect to identify up to 2 coating strategies for improving HADM graft durability leading to successful outcomes in intraperitoneal VHR and up to 2 coating strategies leading to successful outcomes in retrorectus VHR. If both of the tested coating combinations in either study lead to improved repair outcomes compared to untreated controls, we will statistically identify the better of the two as the basis of future development of improved grafts for VHR in that respective location. We do not necessarily expect that the same HADM coating combination will prove best for VHR in both tissue locations, given the unique mesenchymal cell and tissue environment of the intraperitoneal and retrorectus spaces. These studies will allow us to confirm the cell and vascular outcomes that best correlate to clinical and functional success.

Future Directions

Novel hyaluronan and gelatin surface coatings will be used as an innovative approach to confer consistency in biologic graft presentation to the host and as a strategy to potentially improve graft durability leading to successful outcomes in ventral hernia repair. What is learned will broaden our understanding of how biologic biomaterials interact with their local tissue environment, thus guiding pathways of future investigation. Future work will include investigation of biologic graft remodeling and strategies to enhance durability in the more challenging scenarios of ventral hernia repair (e.g., infection, co-morbidities, etc.) as well as other clinical indications of soft tissue repair where grafts are commonly used with limited success, such as for example rotator cuff repair, pelvic organ prolapse or urogynecological reconstruction.

Example 4

The objective of this study was to further demonstrate selective and uniform surface coating of HADM grafts with TS-HA or TS-G and to test the ability of these novel hydrogel coatings to act as a cell-barrier (TS-HA) or cell-attractant (TS-G) on HADM.

We coated HADM grafts (DermaMatrix™, Musculoskeletal Transplant Foundation) with TS-HA or TS-G as follows: A 500 µl solution with 10 mU/µl horseradish peroxidase and either 10 mg/ml TS-HA (0.9-1 MDa MW, LifeCore Biomedical, Chaska, Minn.) or 50 mg/ml TS-G (derived from type A gelatin, 300 Bloom, Sigma-Aldrich) was applied on the epidermal surface of lyophilized 2×2 cm grafts. This rehydration method was intended to concentrate the macromolecular TS-HA or TS-G only on the graft surface. After air-drying, a second application of 500 µl of TS-HA or TS-G solution was performed. Again after air-drying, the hydrogel coatings were crosslinked by rehydration of the entire graft in 10 ml of 0.03% hydrogen peroxide. Grafts were then air-dried, rinsed 10 minutes in ultrapure water, and then washed in ultrapure water overnight. HADM grafts were then seeded with $1 \times 10^5$ primary canine tendon fibroblasts and cultured in DMEM with 10% serum for 3 days, after which grafts were processed routinely, embedded in paraffin, sectioned and stained with hematoxylin and eosin (H&E). Three step-level sections per graft group were evaluated for cell attachment and coating thickness (10 measures per section×3 sections=30 measures per graft group).

Figure 9:
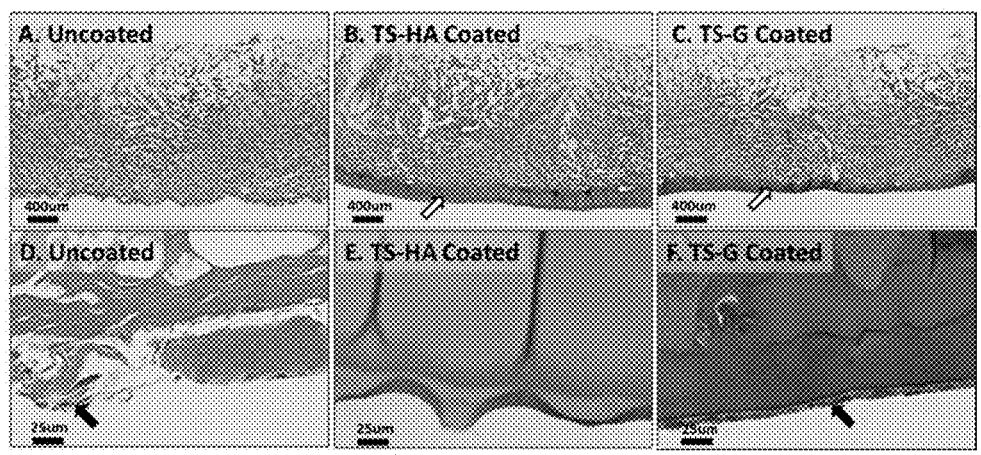
FIG. 9 shows histologic images of HADM. Representative histologic images show uncoated (A, D), TS-HA coated (B, E) and TS-G coated (C, F) HADM. TS-HA and TS-G coatings were localized on only the epidermal surface (B and C, white arrows). No cells were observed on TS-HA coated HADM (E), whereas TS-G coated grafts had a confluent cell layer (F, black arrow). Uncoated HADM showed occasional cell attachment (D, black arrow). Scale bar represents 400 µm (A-C) or 25 µm (D-F).

Results: As intended, the TS-HA or TS-G coatings were effectively localized on only the epidermal surface of the grafts (FIGS. 9 (B) and (C), arrows). TS-HA coatings averaged 174±57 µm and TS-G coatings averaged 145±66 µm. No cells were observed on TS-HA coated HADM (FIG. 9 (E)), whereas TS-G coated grafts had a confluent cell layer (FIG. 9 (F)). Uncoated HADM showed occasional cell attachment (FIG. 9 (D)). This study shows our ability to selectively and uniformly surface coat HADM grafts with TS-HA or TS-G and the ability of these novel hydrogel coatings to act as a cell-barrier (TS-HA) or cell-attractant (TS-G) on HADM.

REFERENCES CITED

1. Bruggeman L A, Doan R P, Loftis J, Darr A, Calabro A. A cell culture system for the structure and hydrogel properties of basement membranes; Application to capillary walls. Cellular and molecular bioengineering. 2012; 5(2):194-204. Epub 2012/10/23. doi: 10.1007/s12195-012-0221-3. PubMed PMID: 23087767; PubMed Central PMCID: PMC3475204.
2. Brochhausen C, Schmitt V H, Rajab T K, Planck C N, Kramer B, Wallwiener M, et al. Intraperitoneal adhesions—an ongoing challenge between biomedical engineering and the life sciences. J Biomed Mater Res A. 2011; 98(1):143-56. Epub 2011/05/07. doi: 10.1002/jbm.a.33083. PubMed PMID: 21548063.
3. Darr A, Calabro A. Synthesis and characterization of tyramine-based hyaluronan hydrogels. Journal of materials science Materials in medicine. 2009; 20(1):33-44. Epub 2008/08/01. doi: 10.1007/s10856-008-3540-0. PubMed PMID: 18668211.
4. Kurisawa M, Chung J E, Yang Y Y, Gao S J, Uyama H. Injectable biodegradable hydrogels composed of hyaluronic acid-tyramine conjugates for drug delivery and tissue engineering. Chemical communications. 2005 (34):4312-4. Epub 2005/08/23. doi: 10.1039/b506989k. PubMed PMID: 16113732.
5. Lee F, Chung J E, Kurisawa M. An injectable hyaluronic acid-tyramine hydrogel system for protein delivery. Journal of controlled release: official journal of the Controlled Release Society. 2009; 134(3):186-93. Epub 2009/01/06. doi: 10.1016/j.jconrel.2008.11.028. PubMed PMID: 19121348.

The invention claimed is:

1. A biocompatible tissue graft comprising:
   (a) a bulk graft comprising a biocompatible material and having at least a first surface, and
   (b) a coating comprising a hydrogel and being immobilized on the bulk graft at the first surface,
   wherein:
   (i) the biocompatible material comprises at least one of a biologic material or a biologic-synthetic composite material, and
   (ii) the hydrogel comprises cross-linked hydroxyphenyl-substituted hyaluronan (HPS-HA), cross-linked hydroxyphenyl-substituted collagen (HPS-C), or both, the cross-linked HPS-HA, cross-linked HPS-C, or both having been formed by cross-linking of hydroxyphenyl groups of HPS-HA, HPS-C, or both to form dihydroxyphenyl bridges.

2. The biocompatible tissue graft of claim 1, wherein the biocompatible tissue graft is a soft tissue graft, a mesenchymal tissue graft, a hernia repair graft, a rotator cuff repair graft, a pelvic organ prolapse repair graft, or a uro-gynecological reconstruction graft.

3. The biocompatible tissue graft of claim 1, wherein the biologic material or biologic-synthetic composite material comprises at least one of an extracellular matrix material, acellular dermis matrix, non-reinforced acellular dermis matrix, reinforced acellular dermis matrix, decellularized small intestinal submucosa, urinary bladder matrix, muscle, fibronectin, fibrin, fibrinogen, collagen, adhesive glycoprotein, proteoglycan, heparin sulfate, chondroitin sulfate, dermatan sulfate, hyaluronan, secreted protein acidic and rich in cysteine (SPARC), thrombospondins, tenacin, a cell adhesion molecule, integrin, vitronectin, fibronectin, laminin, elastin, protein found in basement membranes, fibrosin, albumin, sodium alginate, a derivative of sodium alginate, chitosan, a derivative of chitosan, gelatin, starch, silk, cellulose, methylcellulose, hydroxypropylcellulose, hydroxypropylmethylcellulose, carboxymethylcellulose, cellulose acetate phthalate, cellulose acetate succinate, hydroxypropylmethylcellulose phthalate, casein, dextran, a derivative of dextran, polysaccharides, poly(orthoesters), polyesters, poly (hydroxyvaleric acid), polydioxanone, poly(ethylene terephthalate), poly(malic acid), poly(tartronic acid), polyanhydrides, polyphosphazenes, poly(amino acids), polypropylene (PP), polyurethane (PU), expanded polytetrafluoroethylene (ePTFE), polylactic acid (PLA), polyglycolic acid (PGA), polycaprolactone (PCL), polydioxanone (PDO), trimethylene carbonate (TMC), polyvinyl alcohol (PVA), poly(ethylene oxide), poly(acrylic acid), poly(vinyl alcohol), poly(N-isopropyl acrylamide), poly(vinyl pyrrolidone) (PVP), poly (methacrylic acid), poly(p-styrene carboxylic acid), poly(p-styrenesulfonic acid), poly(vinylsulfonicacid), poly(ethyleneimine), poly(vinylamine), poly(anhydride), poly(HEMA), polyhydroxybutyrate (PHB), copolymers of two or more of the polymers above, or blends of two or more of the polymers above.

4. The biocompatible tissue graft of claim 1, wherein the biologic material or biologic-synthetic composite material comprises at least one of human extracellular matrix material, human acellular dermis matrix, non-reinforced human acellular dermis matrix, or reinforced human acellular dermis matrix.

5. The biocompatible tissue graft of claim 1, wherein the bulk graft has at least one of (i) a thickness of 0.5 to 4.0 mm, (ii) occasional voids corresponding to tracks made by hair follicles, nerves, glands, blood vessels and/or lymph vessels, of approximately 100 µm or less in diameter, or (iii) a density of 0.2 g/cm$^3$ to 0.6 g/cm$^3$.

6. The biocompatible tissue graft of claim 1, the coating being immobilized on the bulk graft at the first surface via the cross-linked HPS-HA, cross-linked HPS-C, or both.

7. The biocompatible tissue graft of claim 1, the coating being immobilized on the bulk graft at the first surface without carboxymethylcellulose immobilization.

8. The biocompatible tissue graft of claim 1, the coating being immobilized on the bulk graft at the first surface without the hydrogel substantially permeating the bulk graft below the first surface.

9. The biocompatible tissue graft of claim 1, wherein the coating has a thickness of 10 µm to 500 µm.

10. The biocompatible tissue graft of claim 1, wherein the bulk graft further has at least a second surface, the second surface being uncoated.

11. The biocompatible tissue graft of claim 1, wherein the bulk graft further has at least a second surface, the coating also being immobilized on the bulk graft at the second surface.

12. The biocompatible tissue graft of claim 1, the hydrogel comprising the cross-linked HPS-HA.

13. The biocompatible tissue graft of claim 12, wherein the cross-linked HPS-HA comprises cross-linked tyramine-substituted hyaluronan (TS-HA), the cross-linked TS-HA having been formed by cross-linking of tyramine groups of TS-HA to form dityramine bridges.

14. The biocompatible tissue graft of claim 12, the HPS-HA from which the cross-linked HPS-HA was formed having had a weight average molecular weight of 0.1 MDa to 10 MDa before having been cross-linked.

15. The biocompatible tissue graft of claim 12, the HPS-HA from which the cross-linked HPS-HA was formed having had a degree of hydroxyphenyl substitution of 0.5% to 15% with respect to carboxyl groups of glucuronic acid residues of HA before having been cross-linked.

16. The biocompatible tissue graft of claim 12, the cross-linked HPS-HA having been cross-linked by treatment with horseradish peroxidase at a concentration, as provided, of 1 mU/µl to 20 mU/µl, and hydrogen peroxide at a concentration, as provided, of 0.03% to 3%.

17. The biocompatible tissue graft of claim 12, wherein:
   (i) the cross-linked HPS-HA comprises cross-linked TS-HA, the cross-linked TS-HA having been formed by cross-linking of tyramine groups of TS-HA to form dityramine bridges;
   (ii) the TS-HA from which the cross-linked TS-HA was formed having had a weight average molecular weight of 0.1 MDa to 10 MDa before having been cross-linked;
   (iii) the TS-HA from which the cross-linked TS-HA was formed having had a degree of tyramine substitution of 0.5% to 15% with respect to carboxyl groups of glucuronic acid residues of HA before having been cross-linked; and
   (iv) the cross-linked TS-HA having been cross-linked by treatment with horseradish peroxidase at a concentration, as provided, of 1 mU/µl to 20 mU/µl, and hydrogen peroxide at a concentration, as provided, of 0.03% to 3%.

18. The biocompatible tissue graft of claim 1, the hydrogel comprising the cross-linked HPS-C.

19. The biocompatible tissue graft of claim 18, wherein the cross-linked HPS-C comprises cross-linked tyramine-substituted collagen (TS-C), the cross-linked TS-C having been formed by cross-linking of tyramine groups of TS-C to form dityramine bridges.

20. The biocompatible tissue graft of claim 18, the HPS-C from which the cross-linked HPS-C was formed having had a Bloom value of 100 to 300 before having been cross-linked.

21. The biocompatible tissue graft of claim 18, the HPS-C from which the cross-linked HPS-C was formed having had a degree of hydroxyphenyl substitution of 4% to 30% calculated as moles of hydroxyphenyl groups per total moles of aspartate and glutamate of collagen before having been cross-linked.

22. The biocompatible tissue graft of claim 18, the cross-linked HPS-C having been cross-linked by treatment with horseradish peroxidase at a concentration, as provided, of 1 mU/μl to 20 mU/μl, and hydrogen peroxide at a concentration, as provided, of 0.03% to 3%.

23. The biocompatible tissue graft of claim 18, wherein:
  (i) the cross-linked HPS-C comprises cross-linked TS-C, the cross-linked TS-C having been formed by cross-linking of tyramine groups of TS-C to form dityramine bridges;
  (ii) the TS-C from which the cross-linked TS-C was formed having had a Bloom value of 100 to 300 before having been cross-linked;
  (iii) the TS-C from which the cross-linked TS-C was formed having had a degree of tyramine substitution of 4% to 30% calculated as moles of tyramine groups per total moles of aspartate and glutamate of collagen before having been cross-linked; and
  (iv) the cross-linked TS-HC having been cross-linked by treatment with horseradish peroxidase at a concentration, as provided, of 1 mU/μl to 20 mU/μl, and hydrogen peroxide at a concentration, as provided, of 0.03% to 3%.

24. The biocompatible tissue graft of claim 1, the hydrogel comprising both the cross-linked HPS-HA and the cross-linked HPS-C.

25. A method of repair of tissue damage in a subject in need thereof, the method comprising surgically implanting the biocompatible tissue graft of claim 1 into a site of the tissue damage in the subject.

26. The method of claim 25, wherein the tissue damage comprises a hernia, a ventral abdominal wall hernia, a rotator cuff injury, a pelvic organ prolapse, or a uro-gynecological injury.

27. The method of claim 25, wherein the site of the tissue damage is a soft tissue, a mesenchymal tissue, an intraperitoneal tissue, a rotator cuff tissue, a pelvic tissue, or a uro-gynecological tissue.

28. The method of claim 25, wherein:
the site of the tissue damage comprises a tissue surface, and
the implanting comprises positioning the biocompatible tissue graft in contact with the tissue surface.

29. The method of claim 25, wherein:
the site of the tissue damage comprises a visceral tissue surface, and
the implanting comprises positioning the coating of the biocompatible tissue graft in contact with the visceral tissue surface.

* * * * *

UNITED STATES PATENT AND TRADEMARK OFFICE
CERTIFICATE OF CORRECTION

PATENT NO. : 10,004,586 B2
APPLICATION NO. : 14/837658
DATED : June 26, 2018
INVENTOR(S) : Kathleen Anne Derwin and Anthony Calabro Page 1 of 1

It is certified that error appears in the above-identified patent and that said Letters Patent is hereby corrected as shown below:

In the Specification

Column 17, Line 59 "$\geq 7\%$" should read --$\geq 70\%$--

Signed and Sealed this
Twenty-fifth Day of September, 2018

Andrei Iancu
*Director of the United States Patent and Trademark Office*